(12) United States Patent
Gao et al.

(10) Patent No.: US 11,459,344 B2
(45) Date of Patent: Oct. 4, 2022

(54) COMPOUND, LIGHT-EMITTING MATERIAL, AND ORGANIC LIGHT-EMITTING DISPLAY PANEL

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Wei Gao, Shanghai (CN); Lei Zhang, Shanghai (CN); Wenpeng Dai, Shanghai (CN); Jinghua Niu, Shanghai (CN); Dongyang Deng, Shanghai (CN)

(73) Assignees: WUHAN TIANMA MICROELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 368 days.

(21) Appl. No.: 16/691,494

(22) Filed: Nov. 21, 2019

(65) Prior Publication Data
US 2020/0339608 A1    Oct. 29, 2020

(30) Foreign Application Priority Data
Apr. 25, 2019  (CN) .......................... 201910340979.X

(51) Int. Cl.
*C07D 409/14*    (2006.01)
*C07F 5/02*      (2006.01)
(Continued)

(52) U.S. Cl.
CPC ............ *C07F 5/027* (2013.01); *C07D 409/14* (2013.01); *C07F 7/0816* (2013.01);
(Continued)

(58) Field of Classification Search
None
See application file for complete search history.

(56) References Cited

U.S. PATENT DOCUMENTS

| 2011/0278552 A1* | 11/2011 | Numata | H01L 51/0062 257/40 |
| 2019/0027693 A1* | 1/2019 | Zysman-Colman | H01L 51/0052 |
| 2019/0341557 A1* | 11/2019 | Lin | C09K 11/06 |

FOREIGN PATENT DOCUMENTS

| CN | 103896973 B | * | 4/2014 | ............. C09K 11/06 |
| CN | 103896973 A | | 7/2014 | |

(Continued)

OTHER PUBLICATIONS

Machine translation of CN-103896973, translation generated Dec. 2021, 10 pages. (Year: 2021).*

(Continued)

*Primary Examiner* — Robert S Loewe
(74) *Attorney, Agent, or Firm* — Alston & Bird LLP

(57) ABSTRACT

The present disclosure describes a compound, a light-emitting material, an organic light-emitting display panel and an organic light-emitting display device. The compound has the structure of Formula I. The light-emitting material comprises any one or a combination of at least two of the compounds. The organic light-emitting display panel comprises an anode and a cathode disposed opposite to each other, and an organic layer disposed between the anode and the cathode. The material of the organic layer comprises any one or a combination of at least two of the compounds. The organic light-emitting display device comprises the organic light-emitting display panel. The compound has an energy level difference between a singlet and a triplet states as (Continued)

$\Delta E_{st} \geq 0.30$ eV, and, when used in an organic light-emitting display panel, can further increase the luminous efficiency of the device.

19 Claims, 2 Drawing Sheets

(51) Int. Cl.
  *C07F 7/08* (2006.01)
  *H01L 51/00* (2006.01)
  *H01L 51/50* (2006.01)
  *H01L 51/52* (2006.01)
(52) U.S. Cl.
  CPC ........ *H01L 51/008* (2013.01); *H01L 51/0061* (2013.01); *H01L 51/0067* (2013.01); *H01L 51/0072* (2013.01); *H01L 51/0074* (2013.01); *H01L 51/0094* (2013.01); *H01L 51/5056* (2013.01); *H01L 51/5072* (2013.01); *H01L 51/5092* (2013.01); *H01L 51/5206* (2013.01); *H01L 51/5221* (2013.01)

(56) References Cited

FOREIGN PATENT DOCUMENTS

| CN | 106467458 A | 3/2017 | |
|---|---|---|---|
| CN | 107986975 A | 5/2018 | |
| WO | WO-2018033087 A1 * | 2/2018 | ........... C07D 209/86 |

OTHER PUBLICATIONS

Machine tranlsation of WO-2018033087, translation generated Dec. 2021, 24 pages. (Year: 2021).*

* cited by examiner

COMPOUND, LIGHT-EMITTING MATERIAL, AND ORGANIC LIGHT-EMITTING DISPLAY PANEL

CROSS-REFERENCE TO RELATED APPLICATIONS

The application claims the benefit of the earlier filing date of Chinese Patent Application No. CN201910340979.X, filed on Apr. 25, 2019 to the CNIPA, the contents of which are incorporated by reference herein in its entirety.

TECHNICAL FIELD

The present disclosure relates to the technical field of organic light-emitting display device, and in particular to organic electroluminescent materials compound in organic light-emitting displays.

BACKGROUND

Organic electroluminescent devices are brighter than liquid crystal devices, have excellent visual effect, and display clearly because they are self-luminous devices. Therefore, they have been actively studied. To realize the practical use of organic electroluminescent devices, various improvements have been made. For example, the function of each layer of the laminated structure has been further defined. Organic light-emitting devices with a substrate on which an anode, a hole injection layer, a hole transport layer, a light-emitting layer, an electron transport layer, an electron injection layer and a cathode are sequentially disposed have obtained high efficiency and durability. In addition, a lot of research has been done to investigate materials used in each layer, especially materials used in the light-emitting layer.

According to the luminescence mechanism, organic light-emitting materials can be roughly classified into four types: conventional fluorescent materials, phosphorescent materials, triplet-triplet annihilation (TTA) materials, and thermally activated delayed fluorescent (TADF) materials. The maximum internal quantum efficiency of traditional fluorescent materials is only 25%. The theoretical maximum internal quantum yield of TTA materials is not more than 62.5%. Although the theoretical maximum internal quantum yield of phosphorescent materials can reach 100%, they usually contain precious metals, which are expensive. In addition, problems such as poor device stability and severe decrease in device efficiency have further largely limited their commercial use in large-scale.

TADF materials can emit light by using energy of both singlet excitons and triplet excitons. The theoretical maximum quantum yield thereof can reach 100%. Thus, the efficiency of devices using TADF materials is much higher than that of those devices using traditional fluorescent materials. Moreover, their luminous efficiency is theoretically equivalent to that of phosphorescent materials. Therefore, the development of novel TADF materials has brought a new direction for the production of high-efficiency fluorescent devices. In addition, TADF materials are mainly organic compounds and no rare-earth metal elements are needed in their production, which results in a lower production cost. Moreover, TADF materials can be chemically modified by various methods. They are novel organic electroluminescent materials with promising applications. However, existing TADF materials are limited and performance thereof needs to be improved. There is an urgent need to develop novel TADF materials that can be used in OLED devices.

Therefore, there is an urgent need to develop more varieties of TADF materials with improved performance, so that the devices may have higher luminous efficiency.

SUMMARY

The present disclosure, in a first aspect, provides a compound, which has the structure of Formula I:

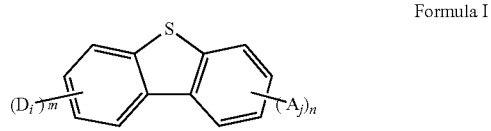

Formula I in Formula I, $D_i$ is any one selected from the group consisting of a substituted or unsubstituted arylamino group, a substituted or unsubstituted carbazole group, a substituted or unsubstituted carbazole derivative group, a substituted or unsubstituted acridine group, and a substituted or unsubstituted acridine derivative group;

in Formula I, $A_j$ is any one selected from an aryl group containing an electron-withdrawing group;

wherein the electron-withdrawing group includes any one or a combination of at least two selected from the group consisting of carbonyl, a sulfone group, phosphoryl a boron atom and imide;

in Formula I, m is an integer from 1 to 4, such as 1, 2, 3, 4, etc., and i is an integer from 1 to m, in Formula I, n is an integer from 1 to 4, such as 1, 2, 3, 4, etc., and j is an integer from 1 to n.

In a second aspect, the present disclosure provides a light-emitting material, which comprises any one or a combination of at least two of the compounds as described in the first aspect.

In a third aspect, the present disclosure provides an organic light-emitting display panel, which comprises an anode and a cathode disposed opposite to each other, and an organic layer disposed between the anode and the cathode;

wherein the material of the organic layer comprises any one or a combination of at least two of the compounds as described in the first aspect.

In a fourth aspect, the present disclosure provides an organic light-emitting display device, which comprises the organic light-emitting display panel as described in the third aspect.

Compared with the related technics, the present disclosure has the following beneficial effects:

(1) The compound provided by the present disclosure has a molecular structure of electron donor-electron acceptor type (D-A type), which facilitates the efficient separation between HOMO and LUMO. The present disclosure uses a substituted or unsubstituted arylamino group, a substituted or unsubstituted carbazole group, a substituted or unsubstituted carbazole derivative group, a substituted or unsubstituted acridine group, or a substituted or unsubstituted acridine derivative group as an electron-donating group, and an aryl group containing a group such as carbonyl, a sulfone group, phosphoryl, a boron atom or imide as an electron-withdrawing group, wherein the electron-donating unit and the electron-withdrawing unit are connected through a benzo five-membered heteroaryl ring, so that the electron cloud of the electron-withdrawing group and that of the electron-donating group have an appropriate degree of overlap, resulting in a low $\Delta E_{st}$ ($\Delta E_{st} \leq 0.30$ eV) and achieving a higher rate constant of reverse intersystem crossing. The compound of the present disclosure makes full use of singlet excitons and triplet excitons to achieve high internal quantum efficiency. When used in an organic light-emitting display panel, the compound of the present disclosure can further improve the luminous efficiency of the device.

(2) In the compound provided by the present disclosure, the spatial restriction effect within the molecule has been increased, which reduces the positive solvation discoloration effect of the molecule, and improve the luminescence color purity of the molecular, thereby achieving a low half peak width.

DETAILED DESCRIPTION

Figure 1:
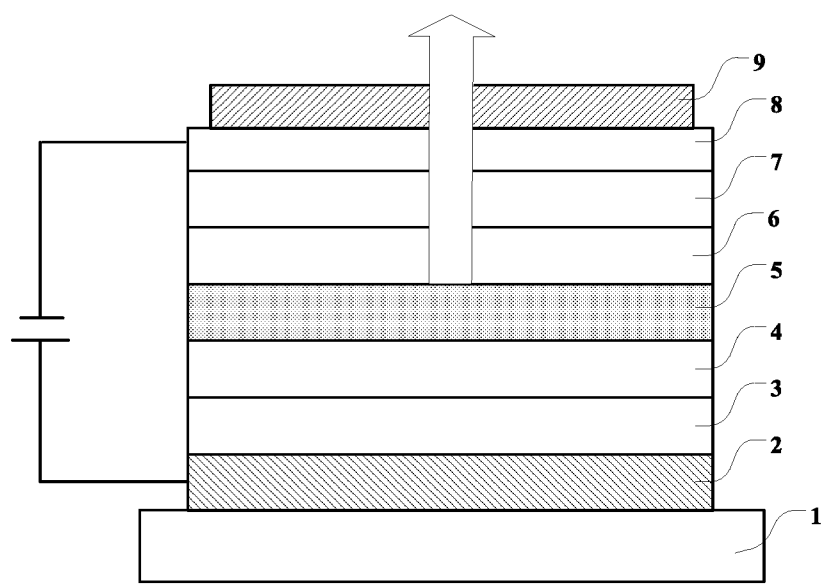
FIG. 1 shows a schematic structural view of an organic light-emitting display panel provided in an embodiment of the present disclosure; wherein: 1—substrate; 2—ITO anode; 3—first hole transport layer; 4—second hole transport layer; 5—light-emitting layer; 6—first electron transport layer; 7—second electron transport layer; 8—magnesium-silver electrode; 9—cap layer.

For the purpose of understanding the present disclosure, the following examples are listed below in the present disclosure. It will be apparent to those skilled in the art that the examples are merely illustrations of the present disclosure and should not be construed as specific limitations to the present disclosure.

In a first aspect, the present disclosure provides a compound, which has the structure of Formula I:

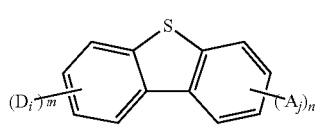

Formula I in Formula I, $D_i$ is any one selected from the group consisting of a substituted or unsubstituted arylamino group, a substituted or unsubstituted carbazole group, a substituted or unsubstituted carbazole derivative group, a substituted or unsubstituted acridine group, and a substituted or unsubstituted acridine derivative group;

in Formula I, $A_j$ is any one selected from an aryl group containing an electron-withdrawing group;

wherein the electron-withdrawing group includes any one or a combination of at least two selected from the group consisting of carbonyl, a sulfone group, a six-membered phosphorus heterocyclic group containing phosphoryl, a boron atom and imide;

in Formula I, m is an integer from 1 to 4, such as 1, 2, 3 or 4, and i is an integer from 1 to m, in Formula I, n is an integer from 1 to 4, such as 1, 2, 3 or 4, and j is an integer from 1 to n.

In Formula I, $D_i$ and $A_j$ are used to represent substituents. $D_i$ and $A_j$ are intended to represent the choice of a group rather than a specific group. When the number of $D_i$ or $A_j$ is greater than or equal to 2, the substituents may be the same or different. Illustratively, if two $D_i$ groups are on the parent group, i.e., m is 2, i is an integer selected from 1 or 2. If i in both $D_i$ is 1, two $D_i$ groups are on the parent group and these two $D_i$ groups are the same. If i in these two $D_i$ is 1 and 2, respectively, $D_1$ and $D_2$ are on the parent group and these two $D_i$ groups may be the same or different.

The compound provided by the present disclosure has a molecular structure of electron donor-electron acceptor type (D-A type), which facilitates the efficient separation between HOMO and LUMO. The present disclosure uses a substituted or unsubstituted arylamino group, a substituted or unsubstituted carbazole group, a substituted or unsubstituted carbazole derivative group, a substituted or unsubstituted acridine group, or a substituted or unsubstituted acridine derivative group as an electron-donating group, and an aryl group containing a group such as carbonyl, a sulfone group, phosphoryl, a boron atom or imide as an electron-withdrawing group, wherein the electron-donating unit and the electron-withdrawing unit are connected through a benzo five-membered heteroaryl ring, so that the electron cloud of the electron-withdrawing group and that of the electron-donating group have an appropriate degree of overlap, resulting in a low $\Delta E_{st}$ ($\Delta E_{st} \leq 0.30$ eV). When used in an organic light-emitting display panel, the compound of the present disclosure can further improve the luminous efficiency of the device.

In the compound provided by the present disclosure, the spatial restriction effect within the molecule has been increased, which reduces the positive solvation discoloration effect of the molecule, and improve the luminescence color purity of the molecular, thereby achieving a low half peak width.

In an embodiment, m≤n.

When the number of the electron-donating group and that of the electron-withdrawing group on the benzo five-membered heteroaryl ring are both 1, the HOMO and LUMO can be effectively separated in space, allowing the compound of the present disclosure to have a low $\Delta E_{st}$ and a high rate constant of reverse intersystem crossing and improving the utilization efficiency of the compound for singlet and triplet excitons; and an appropriate degree of overlap between the HOMO and LUMO is ensured, resulting in a high oscillator strength and allowing the compound to have high luminous efficiency. While ensuring the performance of the compound, the compound has a relative low molecular weight, and it is easier to be deposited by evaporation when used in preparing a device.

In an embodiment, the compound has the structure of Formula II or Formula III;

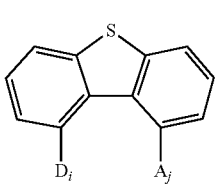

Formula II

-continued

Formula III both i and j are 1;

D$_i$ is any one selected from the group consisting of a substituted or unsubstituted arylamino group, a substituted or unsubstituted carbazole group, a substituted or unsubstituted carbazole derivative group, a substituted or unsubstituted acridine group, and a substituted or unsubstituted acridine derivative group;

A$_j$ is any one selected from an aryl group containing an electron-withdrawing group;

wherein the electron-withdrawing group includes any one or a combination of at least two selected from the group consisting of carbonyl, a sulfone group, phosphoryl, a boron atom and imide.

In the present disclosure, it is preferred that D$_i$ and A$_j$ are attached to the parent core by means of ortho-connection as shown in Formula II or III. Such connection can enhance the dihedral angle between the electron-donating unit D$_i$ and the electron-withdrawing unit A$_j$, so that a large steric hindrance effect is generated between the electron-donating unit D$_i$ and the electron-withdrawing unit A$_j$, thereby obtaining a low $\Delta E_{st}$, and further improving the performance of the compound and improving the luminous efficiency of the device comprising it.

In an embodiment, D$_i$ is selected from wherein # indicates the position at which the group is attached;

a and b are each independently selected from an integer from 0 to 5, such as 0, 1, 2, 3, 4 or 5, e is an integer from 1 to a, and f is an integer from 1 to b, R$_e$ and R$_f$ are each independently any one selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl.

When a or b is 0, the substituent R$_e$ or R$_f$ does not exist, and thus there is no selection range for e or f. Therefore, the range of e or f ranges from 1. The same representation in the following has the same meaning.

In an embodiment, D$_i$ is any one selected from the group consisting of wherein # indicates the position at which the group is attached.

In an embodiment, D$_i$ is any one selected from the group consisting of wherein # indicates the position at which the group is attached;

r and s each is independently selected from an integer from 0 to 4, such as 0, 1, 2, 3, 4, etc., g is an integer from 1 to r, and h is an integer from 1 to s, t is an integer from 0 to 3, such as 0, 1, 2 or 3, and w is an integer from 1 to t, p is an integer from 0 to 2, such as 0, 1 or 2, and v is an integer from 1 to p, Y is any one selected from the group consisting of a carbon atom, a nitrogen atom, an oxygen atom, a sulfur atom, and a silicon atom;

$R_g$, $R_h$, $R_w$ and $R_v$ are each independently any one selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl.

In an embodiment, $D_i$ is any one selected from the group consisting of

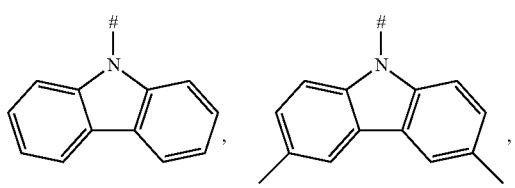

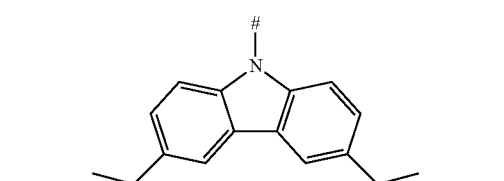

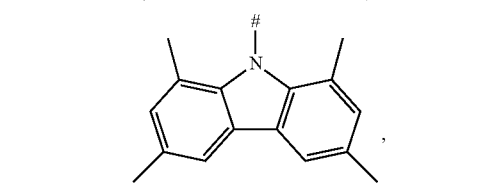

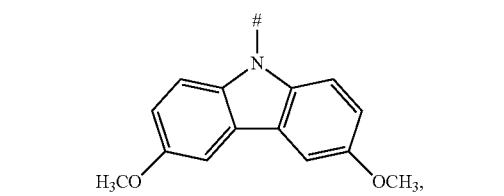

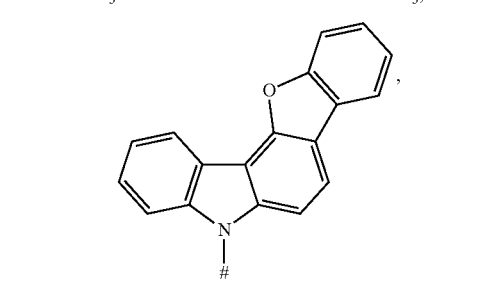

-continued

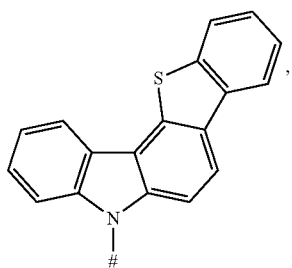

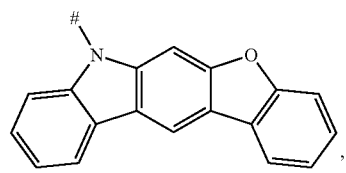

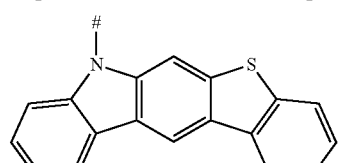

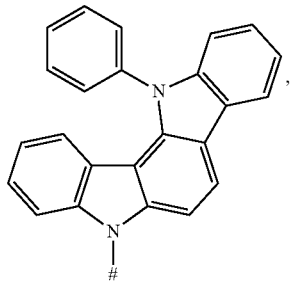

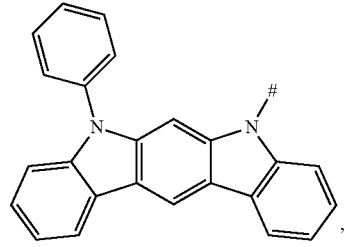

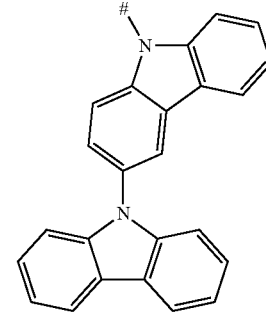

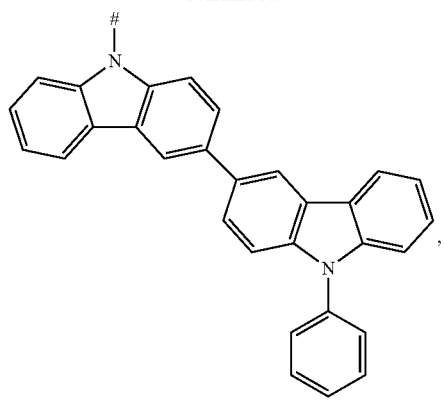
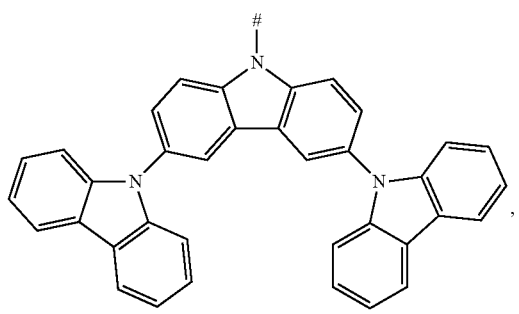
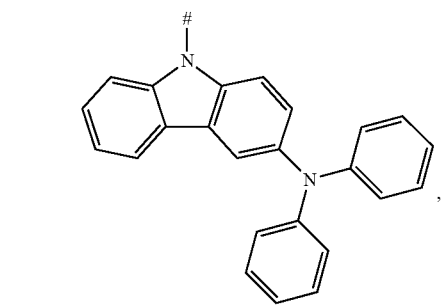
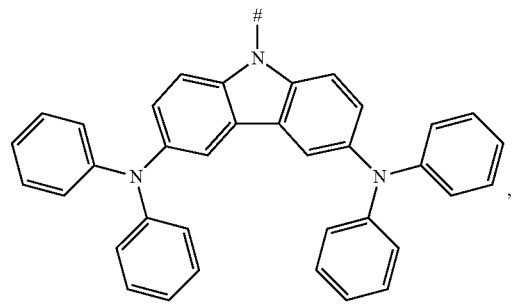
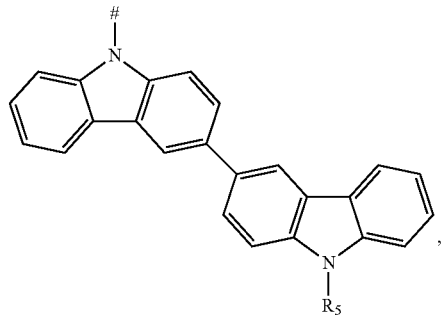
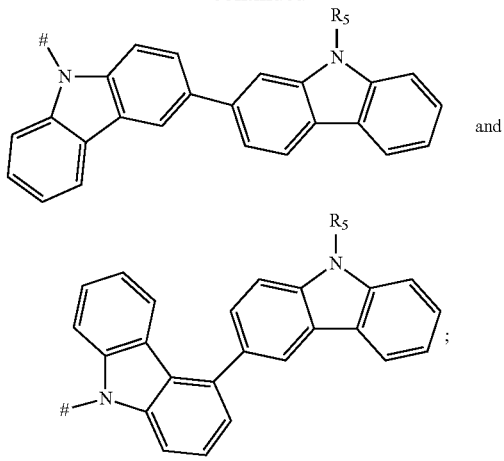
wherein # indicates the position at which the group is attached;
R$_5$ is any one selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl.
In an embodiment, D$_i$ is any one selected from the group consisting of
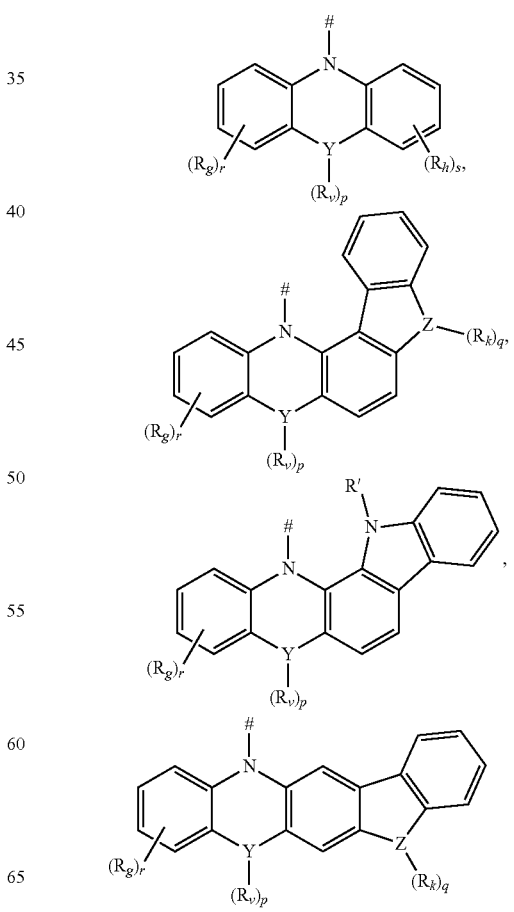

-continued

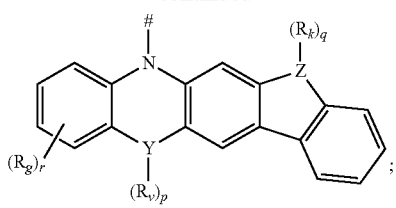

wherein # indicates the position at which the group is attached;

r and s are each independently selected from an integer from 0 to 4, such as 0, 1, 2, 3 or 4, g is an integer from 1 to r, and h is an integer from 1 to s, p and q are each independently selected from an integer from 0 to 2, such as 0, 1 or 2, v is an integer from 1 to p, and k is an integer from 1 to q, Y and Z are each independently any one selected from the group consisting of a carbon atom, a nitrogen atom, an oxygen atom, a sulfur atom, and a silicon atom;

$R'$, $R_g$, $R_v$, $R_h$ and $R_k$ are each independently any one selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl.

In an embodiment, $D_i$ is any one selected from the group consisting of

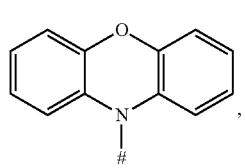, 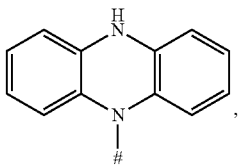,

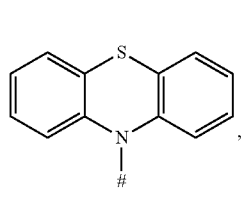, 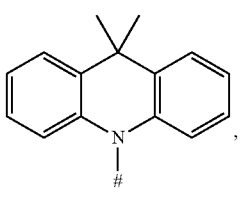,

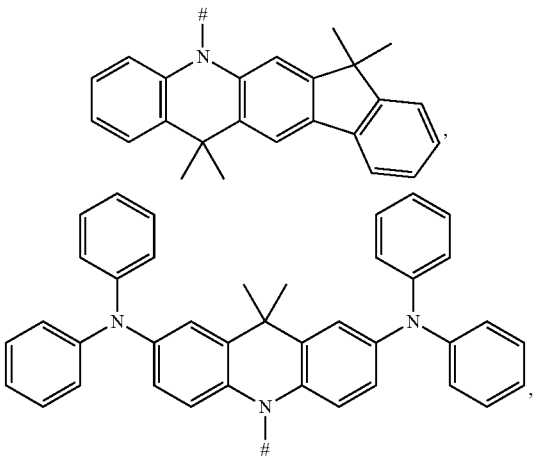

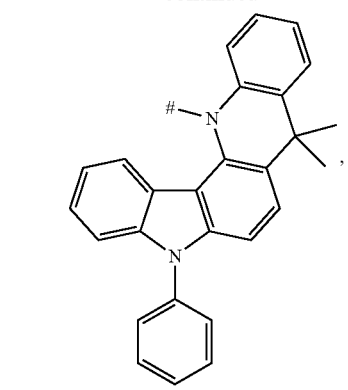,

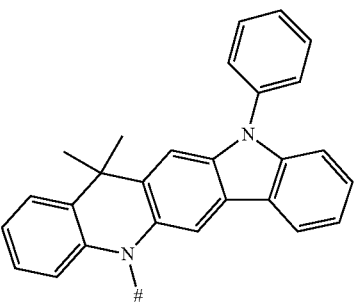 and

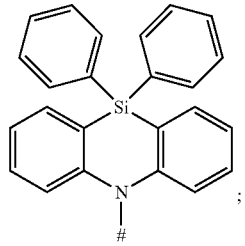;

wherein # indicates the position at which the group is attached.

In an embodiment, the electron-withdrawing group is carbonyl, and $A_j$ is any one selected from the group consisting of

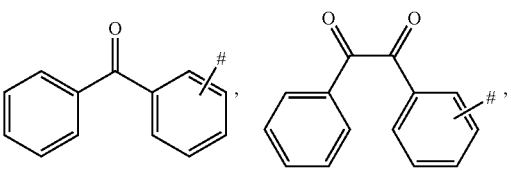

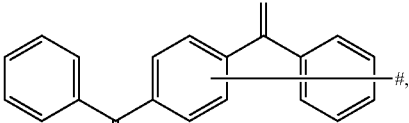

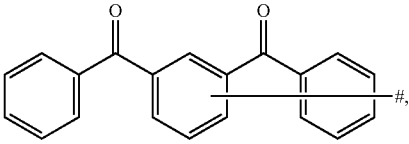

-continued

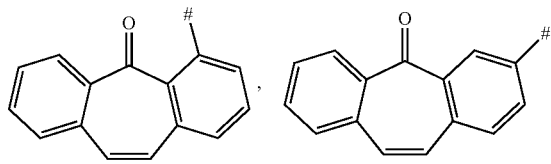

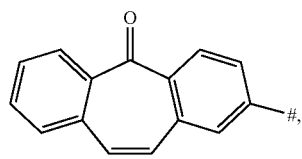

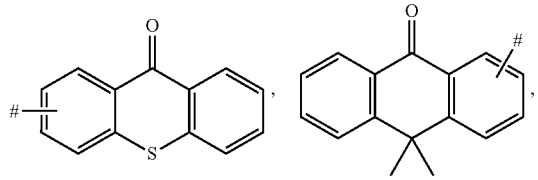

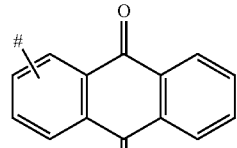

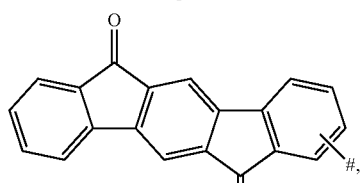

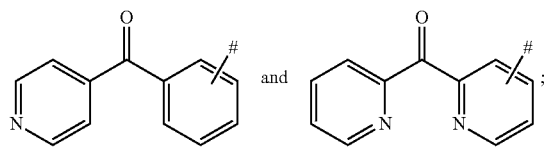

wherein # indicates the position at which the group is attached.

In an embodiment, the electron-withdrawing group is imide, and $A_j$ is any one selected from the group consisting of

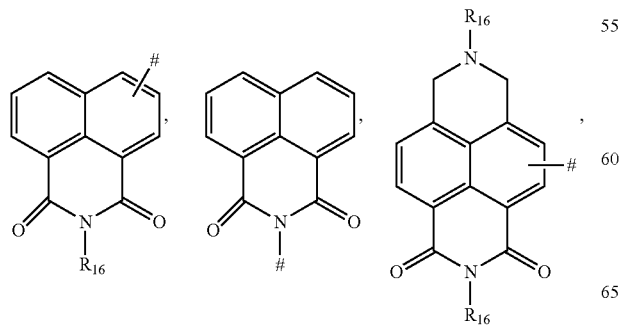

-continued

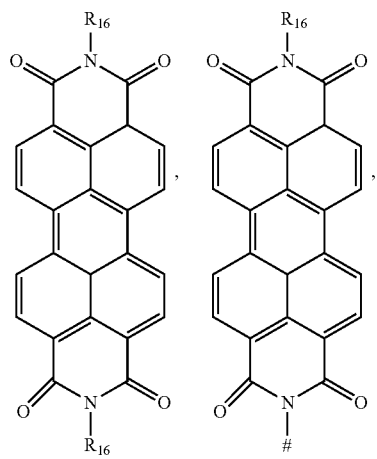

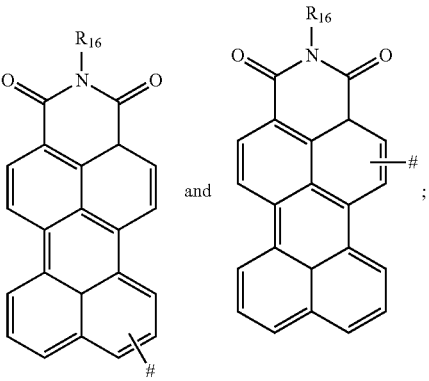

wherein # indicates the position at which the group is attached;

$R_{16}$ is any one selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl.

In an embodiment, the electron-withdrawing group is a sulfone group, and $A_j$ is any one selected from the group consisting of

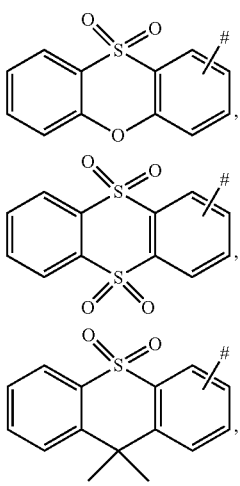

-continued

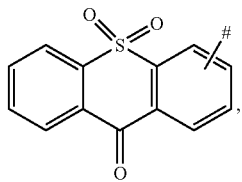,

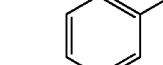,

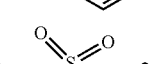 and

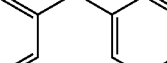;

wherein # indicates the position at which the group is attached.

In an embodiment, the electron-withdrawing group is a six-membered phosphorus heterocyclic group containing phosphoryl, and $A_j$ is any one selected from the group consisting of

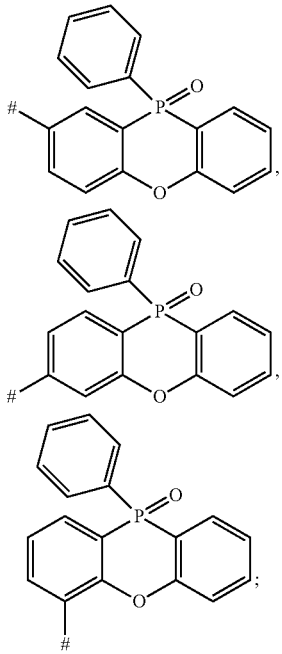

wherein # indicates the position at which the group is attached.

In an embodiment, the electron-withdrawing group is a boron atom, and $A_j$ is any one selected from the group consisting of

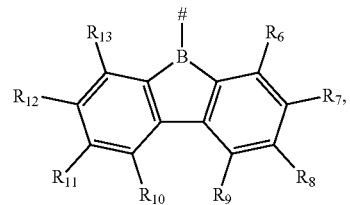

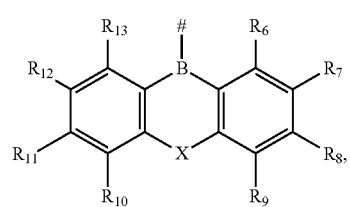

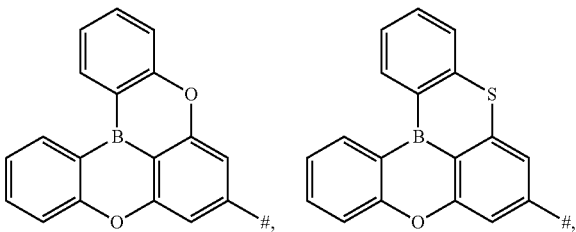

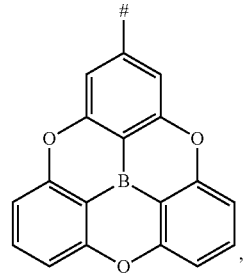,

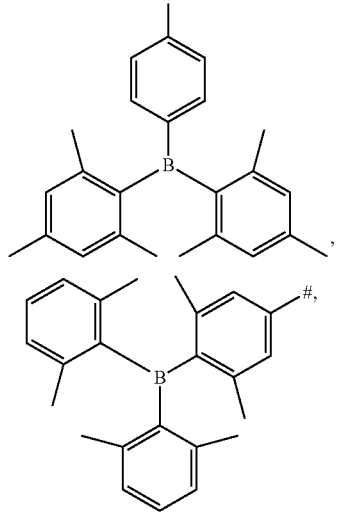

-continued

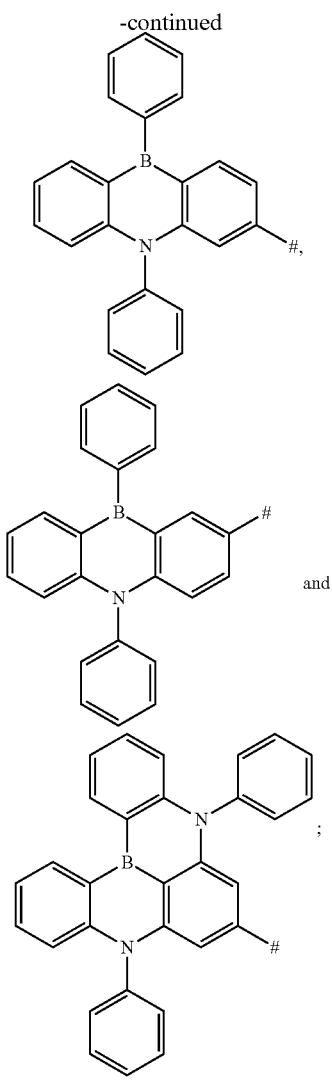

X is any one selected from the group consisting of

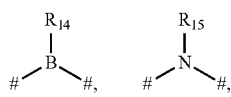

an oxygen atom, and a sulfur atom;

wherein # indicates the position at which the group is attached;

$R_6$, $R_7$, $R_8$, $R_9$, $R_{10}$, $R_{11}$, $R_{12}$, $R_{13}$, $R_{14}$ and $R_{15}$ are each independently any one selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl.

In an embodiment, m is 1, and n is 1.

In an embodiment, the compound has a $\Delta E_{st} = E_{S1} - E_{T1} \geq 0.30$ eV, such as 0.24 eV, 0.23 eV, 0.22 eV, 0.21 eV, 0.20 eV, 0.19 eV, 0.18 eV, 0.17 eV, 0.16 eV, 0.15 eV, 0.14 eV, 0.13 eV, 0.12 eV, 0.11 eV, 0.10 eV, 0.09 eV, 0.08 eV, 0.07 eV, 0.06 eV, 0.05 eV, 0.04 eV, 0.03 eV, 0.02 eV or 0.01 eV, etc.

In an embodiment, the compound is any one selected from the group consisting of compounds P1 to P28 as follows:

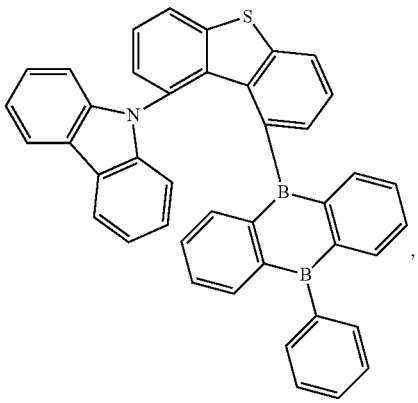
P1

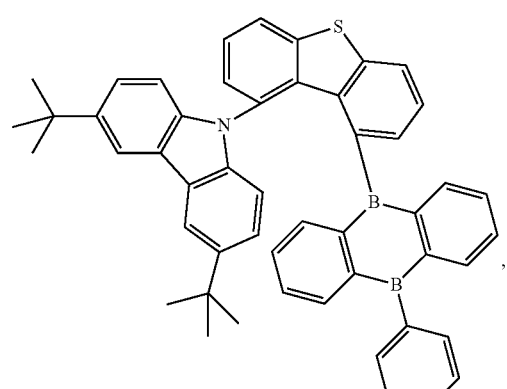
P2

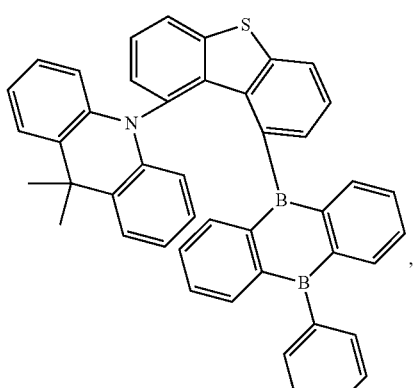
P3

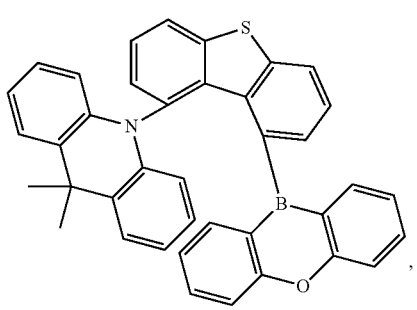
P4

P5
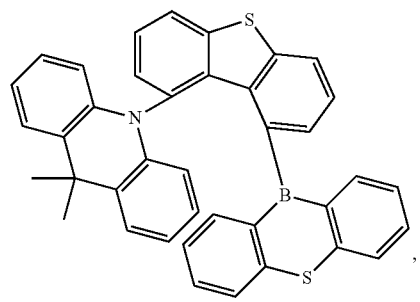
P6
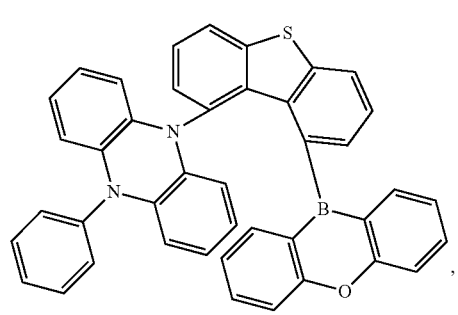
P7
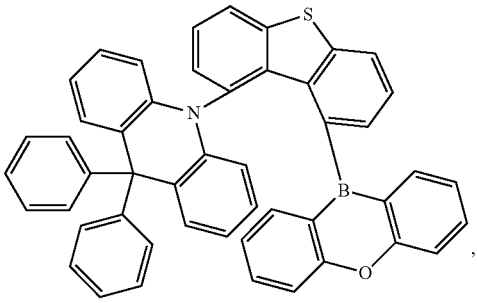
P8
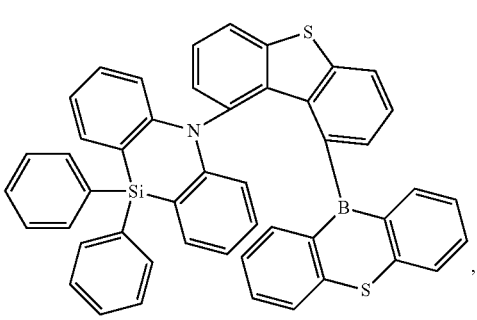
P9
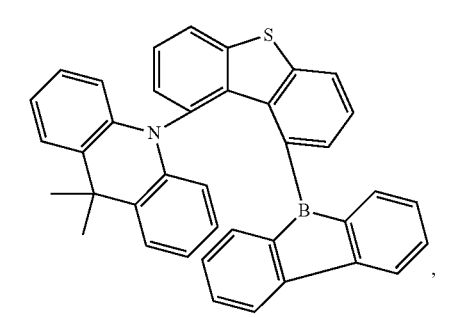
P10
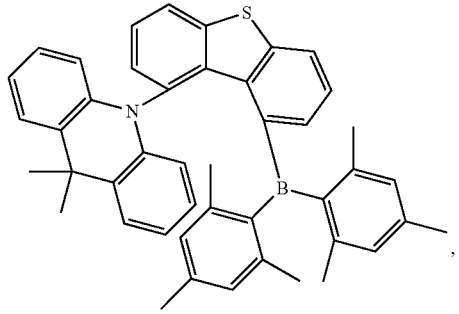
P11
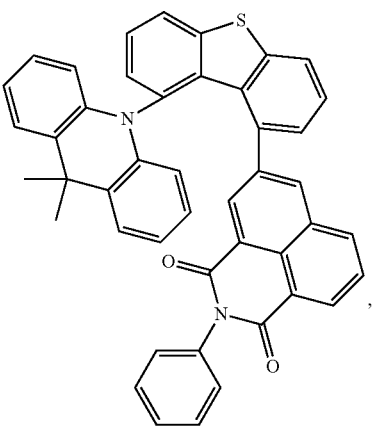
P12
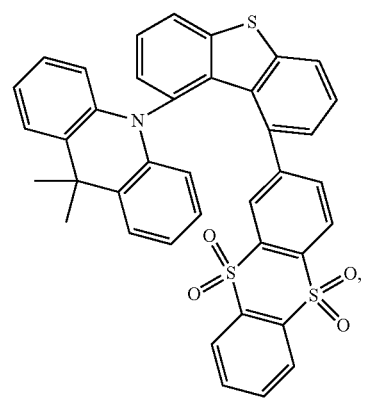

P13
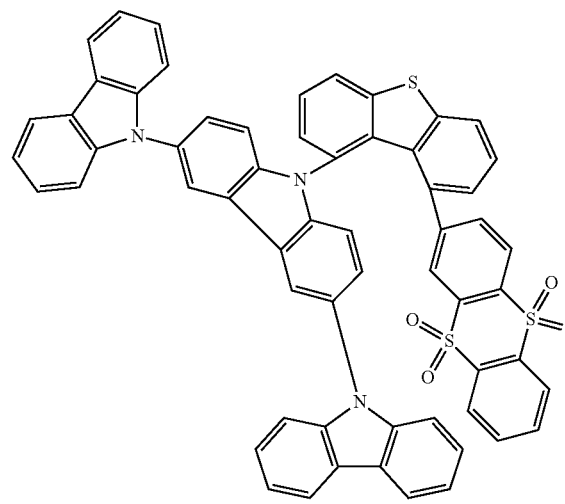
P14
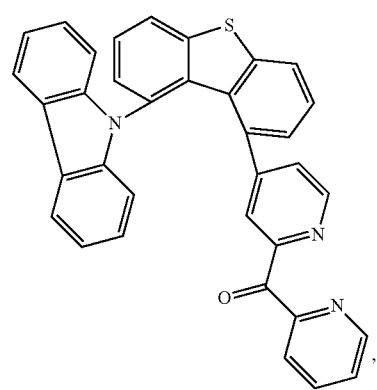
P15
P16
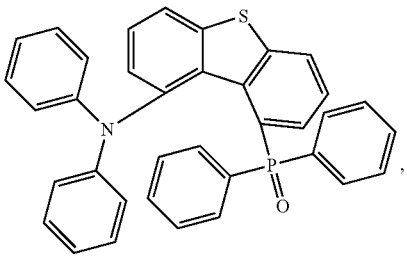
P17
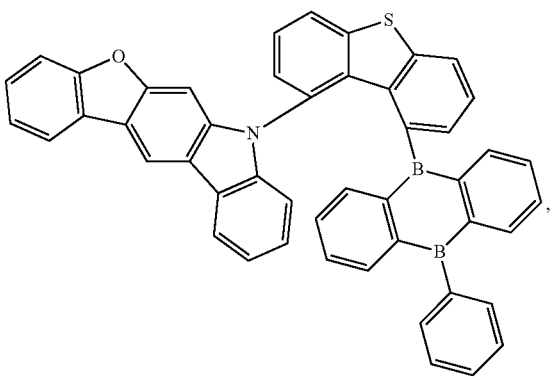
P18
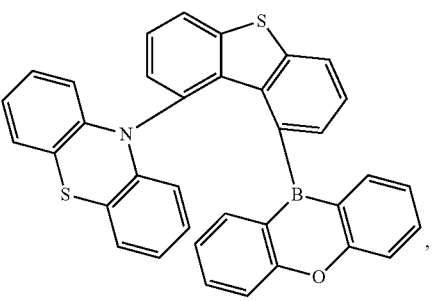
P19
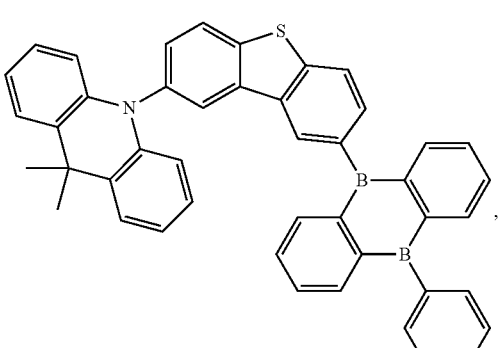
P20
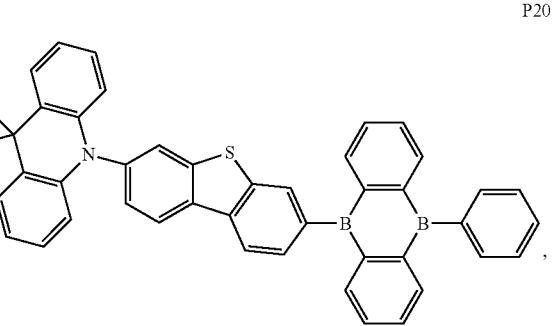

-continued
P21
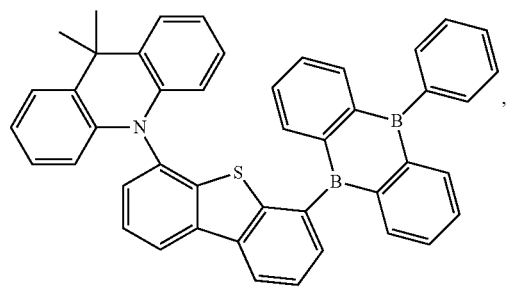
P22
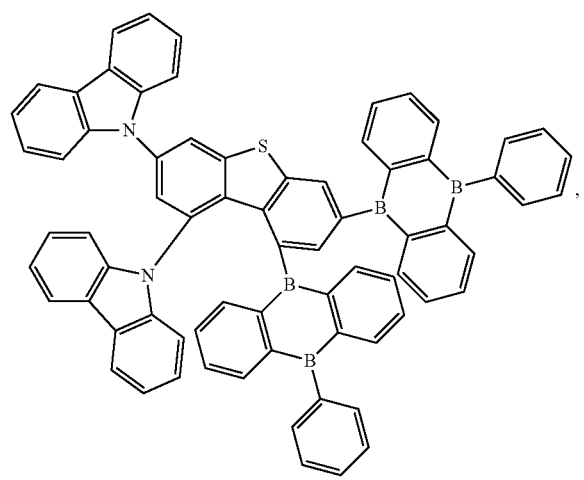
P23
P24
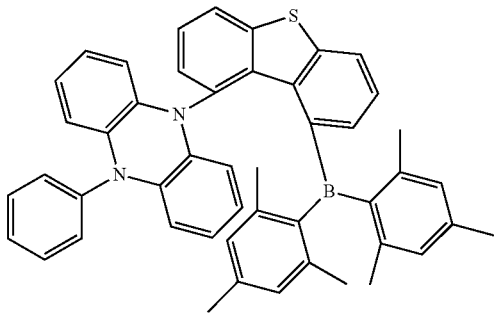
P25
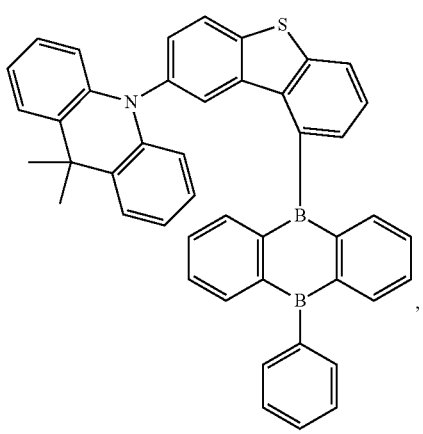
P26
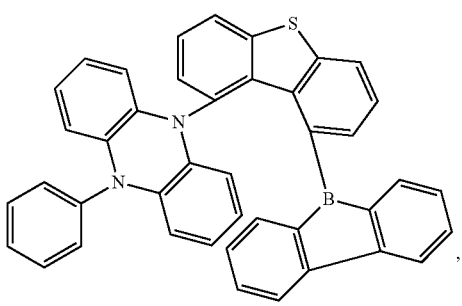
P27
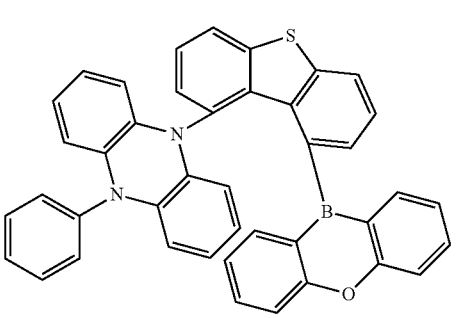
and

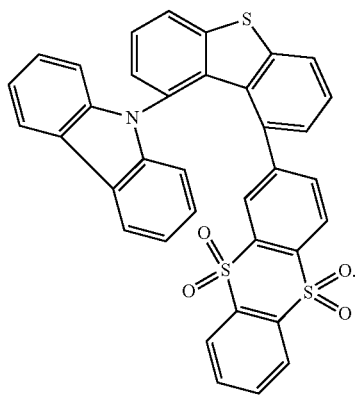
P28

In a second aspect, the present disclosure provides a light-emitting material, which comprises any one or a combination of at least two of the compounds as described in the first aspect.

In a third aspect, the present disclosure provides an organic light-emitting display panel, which comprises an anode and a cathode disposed opposite to each other, and an organic layer disposed between the anode and the cathode; wherein the material of the organic layer comprises any one or a combination of at least two of the compounds as described in the first aspect.

In an embodiment, the organic light-emitting display panel further comprises a cap layer disposed on the side of the cathode facing away from the anode, wherein the material of the cap layer comprises any one or a combination of at least two of the compounds as described in the first aspect.

The organic light-emitting display panel provided by the present disclosure may or may not include a cap layer. When the organic light-emitting display panel is a bottom-emitting OLED device, a cap layer is not required.

In an embodiment, the organic layer comprises any one or a combination of at least two of the group consisting of a hole transport layer, a hole injection layer, an electron blocking layer, a light-emitting layer, a hole blocking layer, an electron transport layer and an electron injection layer.

In an embodiment, the compound is used as a guest material or host material in the organic layer.

In an embodiment, the organic layer comprises a light-emitting layer, wherein the compound is used as a host material or guest material in the light-emitting layer.

An embodiment of the present disclosure provides an organic light-emitting display panel, which comprises an anode and a cathode disposed opposite to each other, and a cap layer disposed on the side of the cathode facing away from the anode, and an organic layer disposed between the anode and the cathode, wherein the organic layer includes a hole transport layer, an electron transport layer and a light emitting layer, wherein the material of at least one of the cap layer and the light-emitting layer is any one or a combination of at least two of the compounds as described above.

In the organic light-emitting display panel provided by the present disclosure, the anode material may be selected from metals such as copper, gold, silver, iron, chromium, nickel, manganese, palladium, platinum, etc., and an alloy thereof. The anode material may also be selected from metal oxides such as indium oxide, zinc oxide, indium tin oxide (ITO), indium zinc oxide (IZO), etc.; the anode material may also be selected from conductive polymers such as polyaniline, polypyrrole, poly(3-methylthiophene), etc. In addition to the anode materials as listed above, the anode material may also be selected from materials that facilitate hole injection, including materials known to be suitable for use as an anode.

In the organic light-emitting display panel provided by the present disclosure, the cathode material may be selected from metals such as aluminum, magnesium, silver, indium, tin, titanium, etc., and an alloy thereof. The cathode material may also be selected from multi-layer metal materials such as LiF/Al, LiO$_2$/Al, BaF$_2$/Al, etc. In addition to the cathode materials as listed above, the cathode material can also be selected from materials that facilitate electron injection, including materials known to be suitable for use as a cathode.

In an embodiment of the present disclosure, the organic light-emitting display panel is prepared by steps of forming an anode on a transparent or non-transparent smooth substrate, forming an organic thin layer on the anode, and forming a cathode on the organic thin layer. The formation of the organic thin layer can be carried out by known film formation methods such as evaporation, sputtering, spin coating, dipping, ion plating and the like. Finally, an organic optical cover layer (also referred as cap layer, CPL) was prepared on the cathode. The material of the optical cover layer CPL is the benzoheterocyclic compound as described in the present disclosure. The optical cover layer CPL can be prepared by evaporation or solution processing. Solution processing methods include ink jet printing, spin coating, knife coating, screen printing, roll-to-roll printing, and the like.

In a fourth aspect, the present disclosure provides an organic light-emitting display device, which comprises the organic light-emitting display panel as described in the third aspect.

The present disclosure provides a method for synthesizing a compound having the structure of Formula I, which is as follows.

Step 1: coupling donor molecule D$_i$ with dibenzothiophene unit Y1 to obtain intermediate Y2, wherein X is a reactive group such as a halogen, a boric acid or a boric acid ester, or a trimethyltin group;

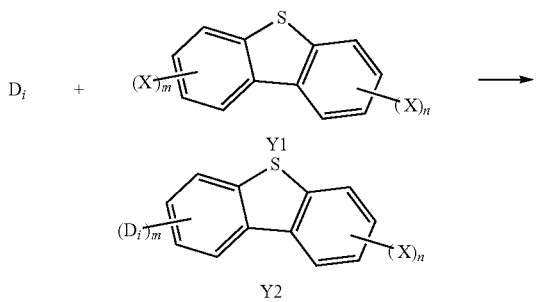

Step 2: coupling the intermediate Y2 with acceptor molecule A$_j$ to obtain the target compound P.

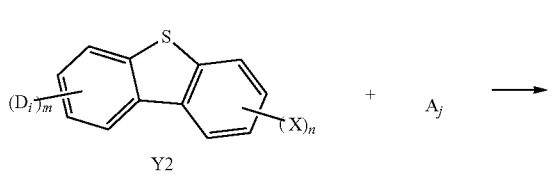

-continued

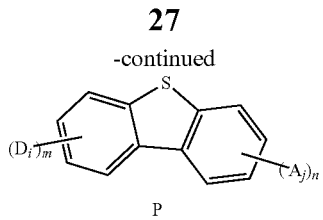

P

The present disclosure provides preparation methods of several exemplary compounds. In the subsequent Preparation Examples, the synthesis of Compounds P1, P2, P3, P10, P24, P25, P26 and P27 is exemplified.

PREPARATION EXAMPLE 1

Compound P1 was prepared by the following method. Specific steps:

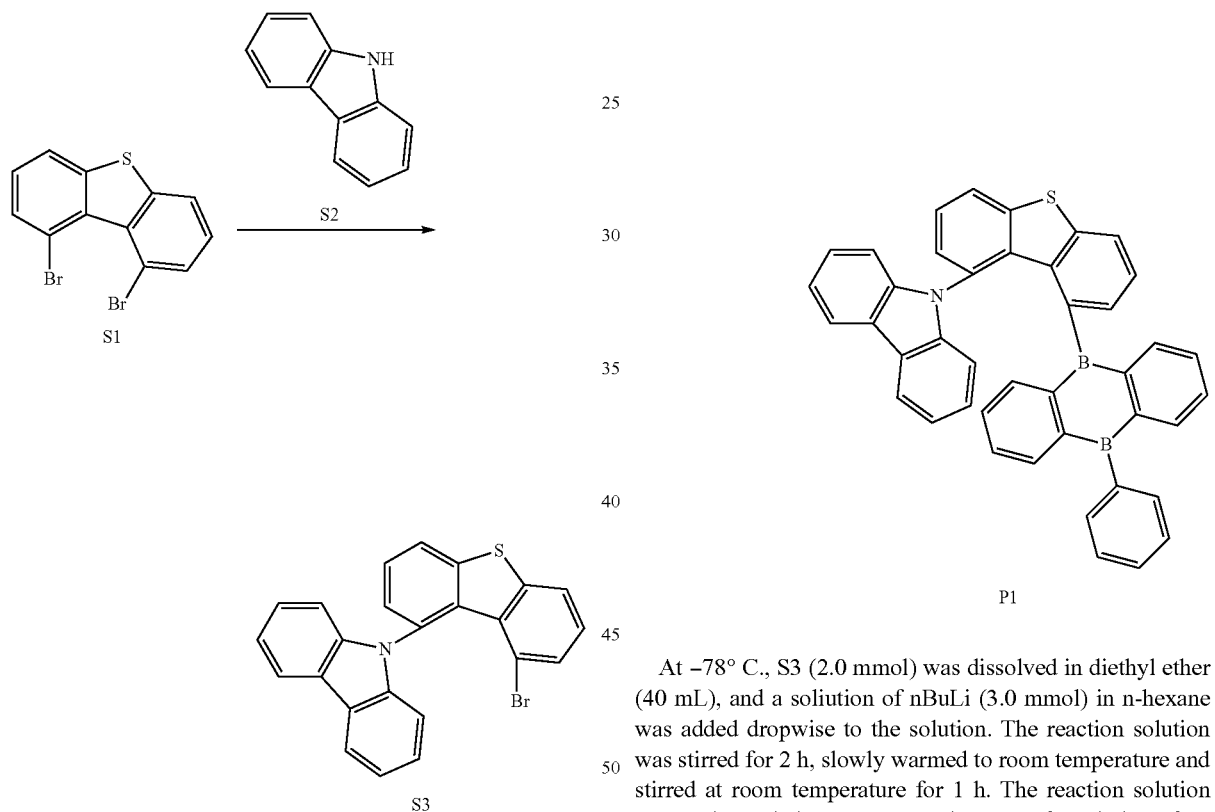

S1 (8.0 mmol), S2 (9.7 mmol), $K_2CO_3$ (33.9 mmol), CuI (2.0 mmol) and 18-crown-6 (0.82 mmol) were weighed and dissolved in anhydrous dichlorobenzene under a nitrogen atmosphere. It was stirred at 100° C. for 12 hours. Upon completion, the reaction mixture was cooled to room temperature, and extracted with dichloromethane. The organic phase was collected and dried over anhydrous $Na_2SO_4$. The dried solution was filtered, and the solvent was removed on a rotary evaporator to give a crude product. The crude product was purified by silica gel column chromatography to obtain S3 as a solid (4.8 mmol, 60%).

Characterization results: MALDI-TOF MS: m/z calcd for $C_{24}H_{14}BrNS$: 427.0; found: 427.3.

At −78° C., S3 (2.0 mmol) was dissolved in diethyl ether (40 mL), and a soliution of nBuLi (3.0 mmol) in n-hexane was added dropwise to the solution. The reaction solution was stirred for 2 h, slowly warmed to room temperature and stirred at room temperature for 1 h. The reaction solution was again cooled to −78° C., and 25 mL of a solution of S4 (2.1 mmol) in toluene was added dropwise with stirring. It was slowly warmed to room temperature and stirred overnight. All solvents were removed by distillation under reduced pressure, and a crude product was collected. The crude product was washed with methanol (3×30 mL) and pentane (3×30 mL), separately, and a crude product was collected again. The crude product was purified by silica gel column chromatography using n-hexane: chloroform (5:1) as an eluent to obtain P1 as a solid (1.64 mmol, 82%).

Characterization results: MALDI-TOF MS: m/z calcd for C42H27B2NS: 599.2; found: 599.6; elemental analysis: calculated: C, 84.17; H, 4.54; B, 3.61; N, 2.34; S, 5.35; found: C, 84.20; H, 4.56; B, 3.59; N, 2.33; S, 5.33.

PREPARATION EXAMPLE 2

Compound P3 was prepared by the following method.

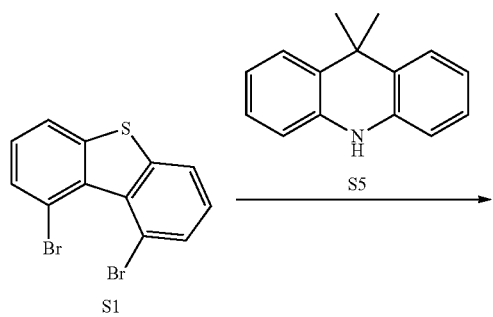

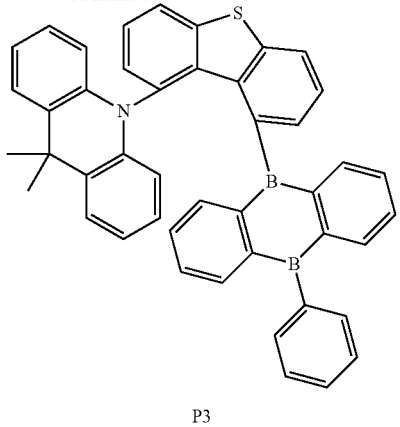

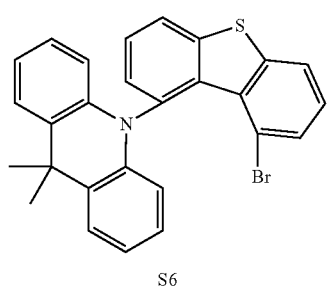

Specific steps:

S1 (6 mmol), S5 (7.2 mmol), K$_2$CO$_3$ (25.2 mmol), CuI (1.5 mmol) and 18-crown-6 (0.64 mmol) were weighed and dissolved in anhydrous dichlorobenzene under a nitrogen atmosphere. It was stirred at 100° C. for 12 hours. Upon completion, the reaction mixture was cooled to room temperature, and extracted with dichloromethane. The organic phase was collected and dried over anhydrous Na$_2$SO$_4$. The dried solution was filtered, and the solvent was removed on a rotary evaporator to give a crude product. The crude product was purified by silica gel column chromatography to obtain S6 as a solid (3.72 mmol, 62%).

Characterization results: MALDI-TOF MS: m/z calcd for C$_{27}$H$_{20}$BrNS: 469.0; found: 469.4.

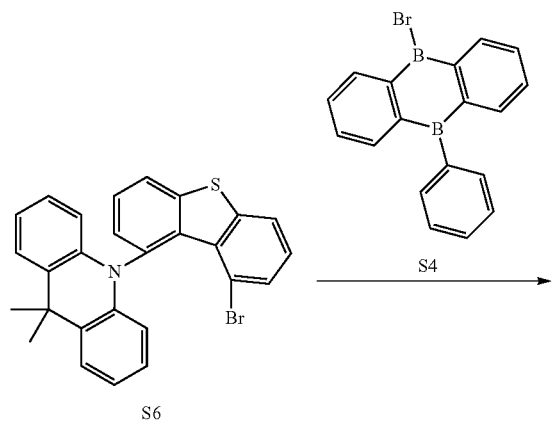

At −78° C., S6 (1.5 mmol) was dissolved in diethyl ether (40 mL), and a solution of nBuLi (2.2 mmol) in n-hexane was added dropwise to the solution. The reaction solution was stirred for 2 h, slowly warmed to room temperature and stirred at room temperature for 1 h. The reaction solution was again cooled to −78° C., and 25 mL of a solution of S4 (1.6 mmol) in toluene was added dropwise with stirring. It was slowly warmed to room temperature and stirred overnight. All solvents were removed by distillation under reduced pressure, and a crude product was collected. The crude product was washed with methanol (3×30 mL) and pentane (3×30 mL), separately, and a crude product was collected again. The crude product was purified by silica gel column chromatography using n-hexane: chloroform (5:1) as an eluent to obtain P3 as a solid (1.12 mmol, 75%).

Characterization results: MALDI-TOF MS: m/z calcd for C$_{45}$H$_{33}$B$_2$NS: 641.2; found: 541.5; elemental analysis: calculated: C, 84.26; H, 5.19; B, 3.37; N, 2.18; S, 5.00; found: C, 84.30; H, 5.20; B, 3.35; N, 2.16; S, 4.99.

PREPARATION EXAMPLE 3

Compound P11 was prepared by the following method.

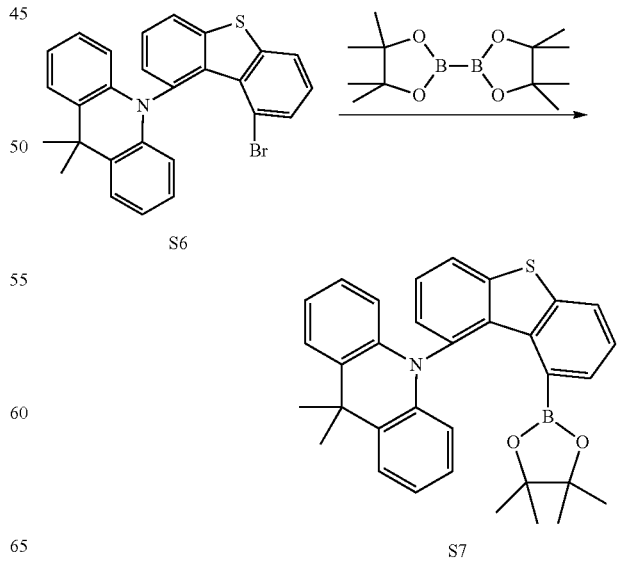

In a 100 mL three-necked flask, S6 (10.0 mmol), bis(pinacolato)diboron (10.5 mmol), (1,1-bis(diphenylphosphino) ferrocene) dichloropalladium (II) (0.2 mmol) and potassium acetate (25.0 mmol) were added separately. The mixture was quickly degassed and replaced with nitrogen 3 times under stirring. 50 mL of tetrahydrofuran was then added by a syringe. Under stirring at a certain rotation speed, the obtained mixture solution was heated and refluxed at 80° C. for 5 h. Upon completion, the reaction was cooled to room temperature, and 60 mL of water was added thereto. The mixture was extracted with diethyl ether. The obtained organic phase was dried over anhydrous sodium sulfate. The solvent was removed by distillation, and the residue was purified by column chromatography to afford Intermediate S7 (7.7 mmol, 77%).

Characterization results: MALDI-TOF MS: m/z calcd for $C_{33}H_{32}BNO_2S$: 517.2; found: 517.3;

Under nitrogen protection, compounds S8 (4.8 mmol), S7 (5.7 mmol), [Pd$_2$(dba)$_3$]·CHCl$_3$ (0.1 mmol) and HP(tBu)$_3$·BF$_4$ (0.2 mmol) were weighed and added to a 100 mL two-necked flask. Into the two-necked flask, 45 mL of toluene (pre-purged with N$_2$ for 15 min to remove oxygen) was poured, then 4 mL of 1 M K$_2$CO$_3$ aqueous solution (pre-purged with N$_2$ for 15 min to remove oxygen) was added dropwise, and the mixture was stirred at room temperature overnight. Upon completion, to the reaction mixture was added 35 mL of deionized water and a few drops of 2 M HCl, and then extracted with dichloromethane. The organic phase was collected and dried over anhydrous Na$_2$SO$_4$. The dried solution was filtered, and the solvent was removed on a rotary evaporator to give a crude product. The crude product was purified by silica gel column chromatography to obtain P11 as a solid (3.94 mmol, 82%).

Characterization results: MALDI-TOF MS: m/z calcd for $C_{45}H_{30}N_2O_2S$: 662.2; found: 662.4; elemental analysis: calculated: C, 81.55; H, 4.56; N, 4.23; O, 4.83; S, 4.84; found: C, 81.58; H, 4.58; N, 4.21; O, 4.82; S, 4.82.

PREPARATION EXAMPLE 4

Compound P14 was prepared by the following method.

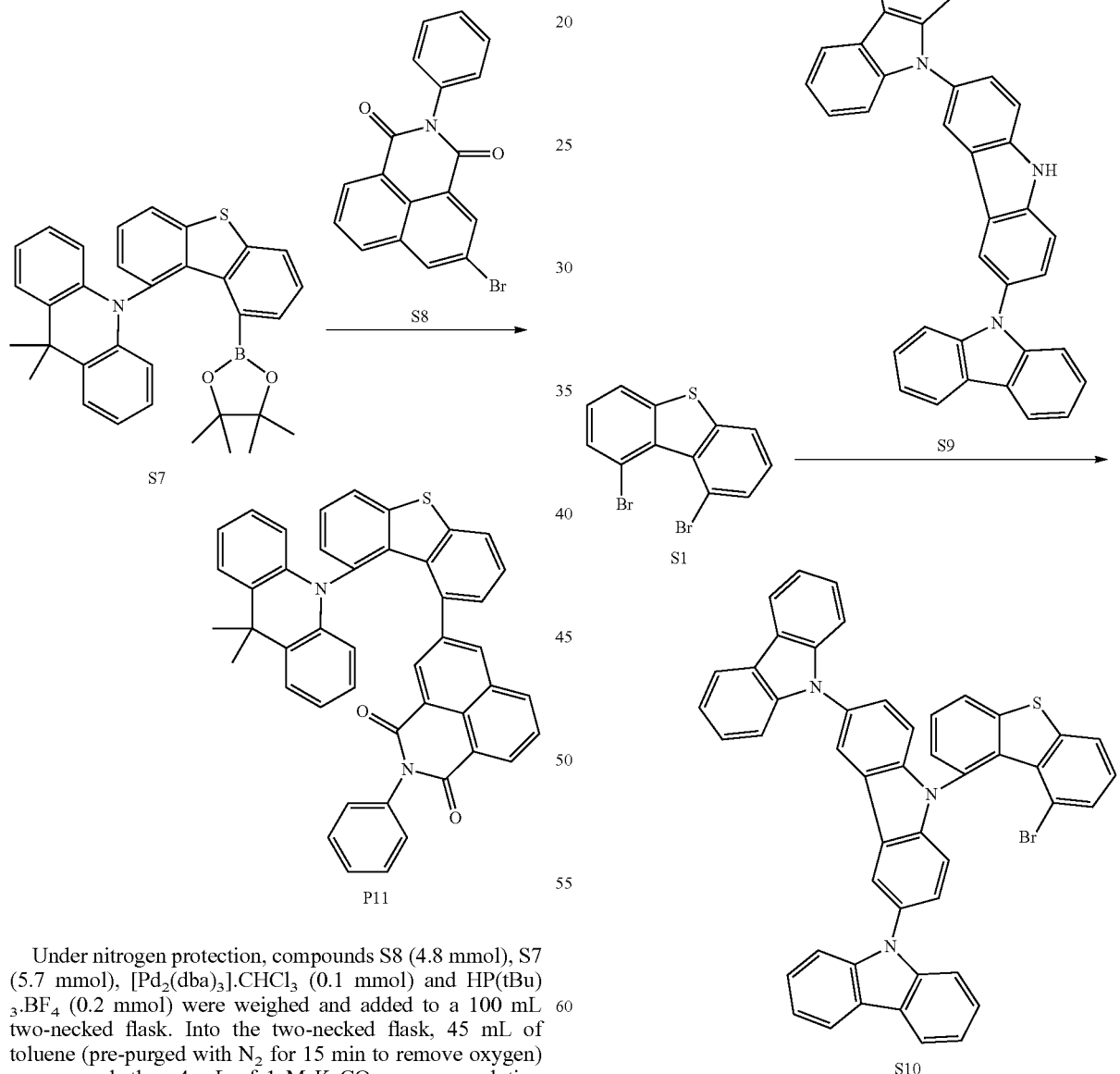

Specific steps:

S1 (5.2 mmol), S9 (6.3 mmol), K$_2$CO$_3$ (21.8 mmol), CuI (1.3 mmol) and 18-crown-6 (0.56 mmol) were weighed and dissolved in anhydrous dichlorobenzene under a nitrogen atmosphere. It was stirred at 100° C. for 12 hours. Upon completion, the reaction mixture was cooled to room temperature, and extracted with dichloromethane. The organic phase was collected and dried over anhydrous $Na_2SO_4$. The dried solution was filtered, and the solvent was removed on a rotary evaporator to give a crude product. The crude product was purified by silica gel column chromatography to obtain S10 as a solid (3.0 mmol, 58%).

Characterization results: MALDI-TOF MS: m/z calcd for $C_{48}H_{28}BrN_3S$: 757.1; found: 757.4;

Characterization results: MALDI-TOF MS: m/z calcd for $C_{54}H_{40}BN_3O_2S$: 805.3; found: 805.5;

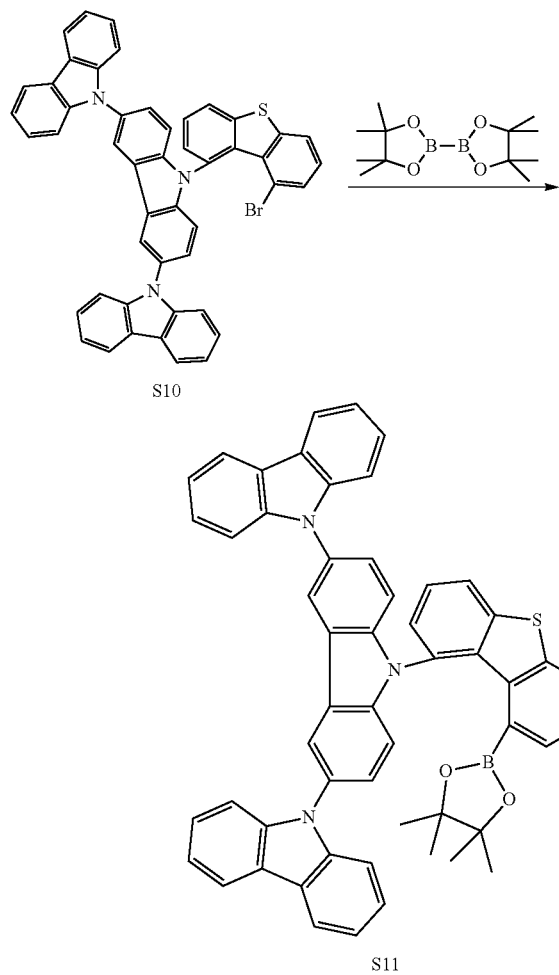

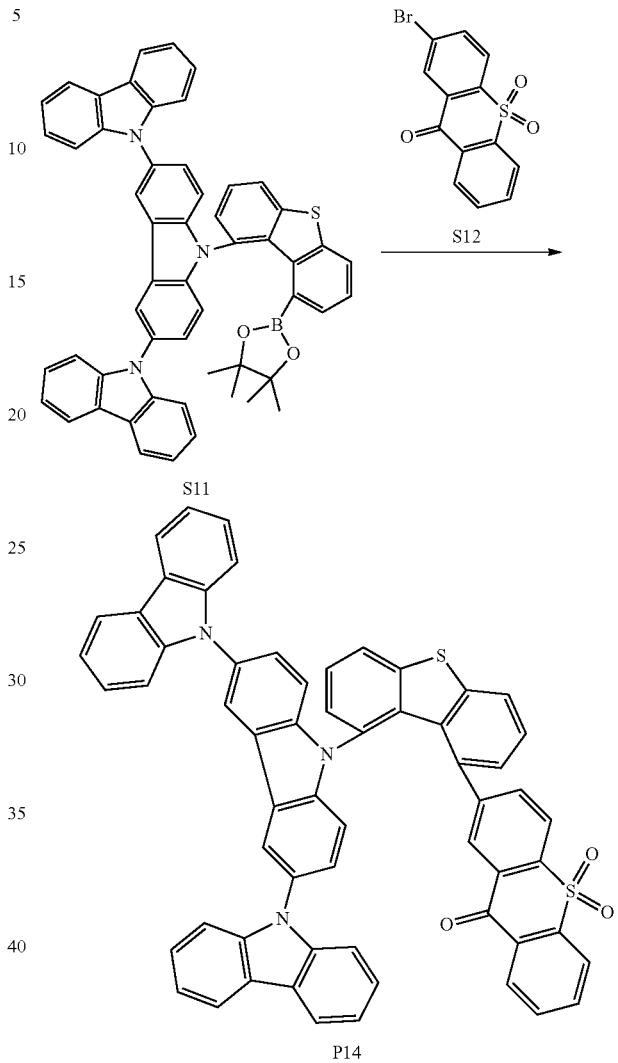

In a 100 mL three-necked flask, S10 (5.0 mmol), bis(pinacolato)diboron (5.2 mmol), (1,1-bis(diphenylphosphino) ferrocene) dichloropalladium (II) (0.05 mmol) and potassium acetate (12.5 mmol) were added separately. The mixture was quickly degassed and replaced with nitrogen 3 times under stirring. 40 mL of tetrahydrofuran was then added by a syringe. Under stirring at a certain rotation speed, the obtained mixture solution was heated and refluxed at 80° C. for 5 h. Upon completion, the reaction was cooled to room temperature, and 60 mL of water was added thereto. The mixture was extracted with diethyl ether. The obtained organic phase was dried over anhydrous sodium sulfate. The solvent was removed by distillation, and the residue was purified by column chromatography to afford Intermediate S11 (4.0 mmol, 80%).

Under nitrogen protection, compounds S12 (7.5 mmol), S11 (8.0 mmol), $[Pd_2(dba)_3]·CHCl_3$ (0.2 mmol) and $HP(tBu)_3·BF_4$ (0.4 mmol) were weighed and added to a 100 mL two-necked flask. Into the two-necked flask, 50 mL of toluene (pre-purged with $N_2$ for 15 min to remove oxygen) was poured, then 6 mL of 1 M $K_2CO_3$ aqueous solution (pre-purged with $N_2$ for 15 min to remove oxygen) was added dropwise, and the mixture was stirred at room temperature overnight. Upon completion, to the reaction mixture was added 50 mL of deionized water and a few drops of 2 M HCl, then extracted with dichloromethane. The organic phase was collected and dried over anhydrous $Na_2SO_4$. The dried solution was filtered, and the solvent was removed on a rotary evaporator to give a crude product. The crude product was purified by silica gel column chromatography to obtain P14 as a solid (5.1 mmol, 68%).

Characterization results: MALDI-TOF MS: m/z calcd for $C_{61}H_{35}N_3O_3S_2$: 921.2; found: 921.5; elemental analysis: calculated: C, 79.46; H, 3.83; N, 4.56; O, 5.21; S, 6.95; found: C, 79.50; H, 3.84; N, 4.54; O, 5.19; S, 6.94.

PREPARATION EXAMPLE 5

Compound P15 was prepared by the following method.

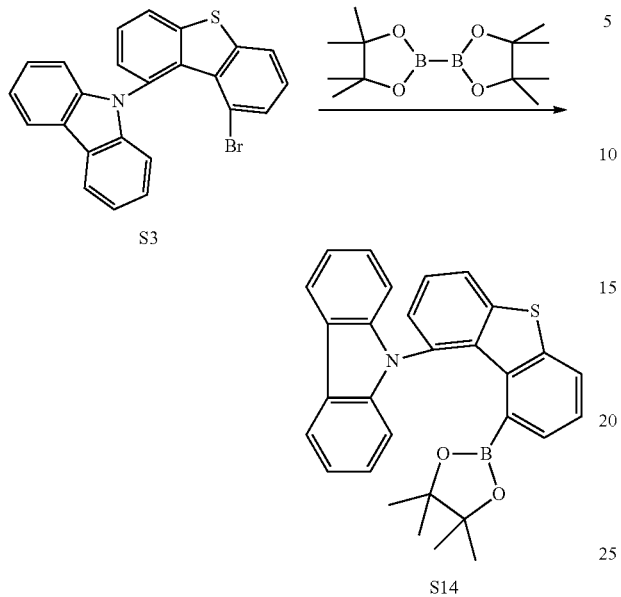

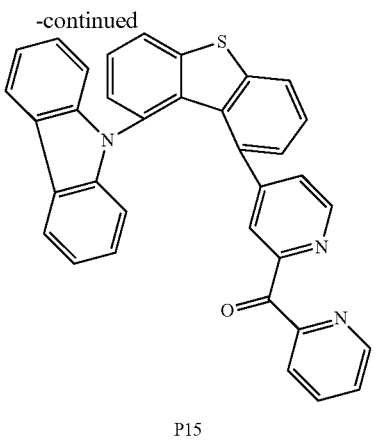

In a 100 mL three-necked flask, S3 (6.0 mmol), bis(pinacolato)diboron (6.4 mmol), (1,1-bis(diphenylphosphino) ferrocene) dichloropalladium (II) (0.08 mmol) and potassium acetate (15.0 mmol) were added separately. The mixture was quickly degassed and replaced with nitrogen 3 times under stirring. 40 mL of tetrahydrofuran was then added by a syringe. Under stirring at a certain rotation speed, the obtained mixture solution was heated and refluxed at 80° C. for 5 h. Upon completion, the reaction was cooled to room temperature, and 50 mL of water was added thereto. The mixture was extracted with diethyl ether. The obtained organic phase was dried over anhydrous sodium sulfate. The solvent was removed by distillation, and the residue was purified by column chromatography to afford Intermediate S14 (4.92 mmol, 82%).

Characterization results: MALDI-TOF MS: m/z calcd for $C_{30}H_{26}BNO_2S$: 475.2; found: 475.6;

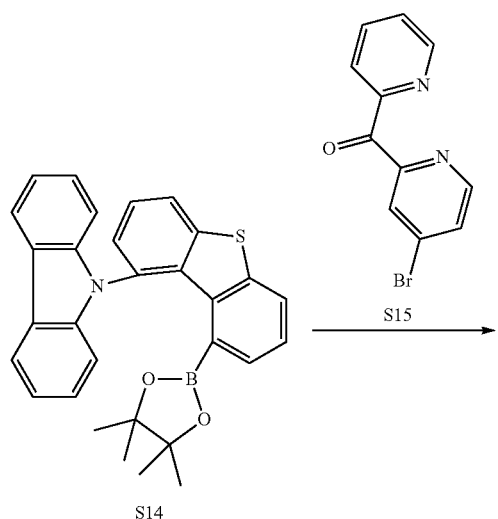

Under nitrogen protection, compounds S15 (4.5 mmol), S14 (5.9 mmol), $[Pd_2(dba)_3] \cdot CHCl_3$ (0.1 mmol) and $HP(tBu)_3 \cdot BF_4$ (0.2 mmol) were weighed and added to a 100 mL two-necked flask. Into the two-necked flask, 50 mL of toluene (pre-purged with $N_2$ for 15 min to remove oxygen) was poured, then 4 mL of 1 M $K_2CO_3$ aqueous solution (pre-purged with $N_2$ for 15 min to remove oxygen) was added dropwise, and the mixture was stirred at room temperature overnight. Upon completion, to the reaction mixture was added 45 mL of deionized water and a few drops of 2 M HCl, then extracted with dichloromethane. The organic phase was collected and dried over anhydrous $Na_2SO_4$. The dried solution was filtered, and the solvent was removed on a rotary evaporator to give a crude product. The crude product was purified by silica gel column chromatography to obtain P15 as a solid (3.8 mmol, 84%).

Characterization results: MALDI-TOF MS: m/z calcd for $C_{35}H_{21}N_3OS$: 531.1; found: 531.5; elemental analysis: calculated: C, 79.07; H, 3.98; N, 7.90; O, 3.01; S, 6.03; found: C, 79.10; H, 4.00; N, 7.88; O, 3.00; S, 6.01.

Organic Light-Emitting Display Panel

In order to facilitate the understanding of the present disclosure, the present disclosure exemplifies examples of the organic light emitting display panel. It should be understood by those skilled in the art that the examples are only intended to help the understanding of the present disclosure and should not be construed as limitation thereto.

As shown in FIG. 1, another aspect of the present disclosure provides an organic light-emitting display panel, which comprises a substrate 1, an ITO anode 2, a first hole transport layer 3, a second hole transport layer 4, a light-emitting layer 5, a first electron transport layer 6, a second electron transport layer 7, a magnesium-silver electrode 8 (with a magnesium to silver mass ratio of 9:1) and a cap layer (CPL) 9, wherein the thickness of the ITO anode 2 was 15 nm, the thickness of the first hole transport layer 3 was 10 nm, the thickness of the second hole transport layer 4 was 110 nm, the thickness of the light-emitting layer 5 was 30 nm, the thickness of the first electron transport layer 6 was 30 nm, the thickness of the second electron transport layer 7 was 5 nm, the thickness of the magnesium-silver electrode 8 was 15 nm, and the thickness of the cap layer (CPL) 9 was 100 nm.

EXAMPLE 1

In this embodiment, the compound of the present disclosure was used as a green-red light host material to prepare organic light-emitting display panel N1. The specific preparation steps are as follows.

1) A glass substrate was cut into a size of 50 mm×50 mm×0.7 mm, sonicated in isopropanol and deionized water for 30 minutes, separately, and then exposed to ozone for about 10 minutes for cleaning. The obtained glass substrate with an indium tin oxide (ITO) anode was mounted on a vacuum deposition equipment;

2) A hole injection layer material HAT-CN having a thickness of 10 nm was deposited on the ITO anode layer 2 by vacuum evaporation and was used as a hole injection layer 3;

3) A second hole transport layer material TAPC having a thickness of 110 nm was deposited on the hole injection layer 3 by vacuum evaporation and was used as a hole transport layer 4;

4) A light-emitting layer 5 having a thickness of 30 nm was deposited on the hole transport layer 4 by vacuum evaporation, wherein Compound P1 of the present disclosure was used as a host material, and Ir(ppy)$_3$ was used as a dopant material with a doping ratio of 8% (mass ratio);

5) A first electron transport layer TPBI having a thickness of 30 nm was deposited on the light-emitting layer 5 by vacuum evaporation and was used as an electron transport layer 6;

6) A second electron transport layer Alq$_3$ having a thickness of 5 nm was deposited on the electron transport layer 6 by vacuum evaporation and was used as an electron injection layer 7;

7) A magnesium-silver electrode having a Mg:Ag ratio of 9:1 and a thickness of 15 nm was deposited on the electron injection layer 7 by vacuum evaporation and was used as a cathode;

8) A HT layer having a thickness of 100 nm was deposited on the cathode 8 by vacuum evaporation and was used as a cap layer (CPL).

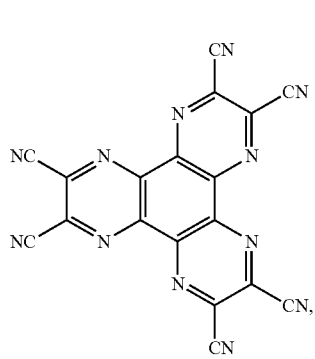

HAT-CN

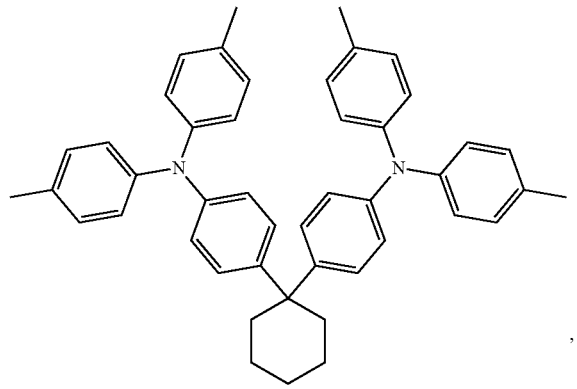

TAPC

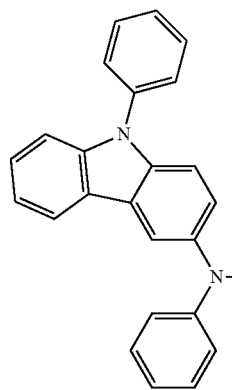

HT

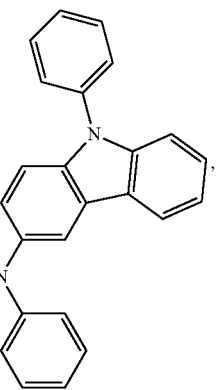

Ir(ppy)$_3$

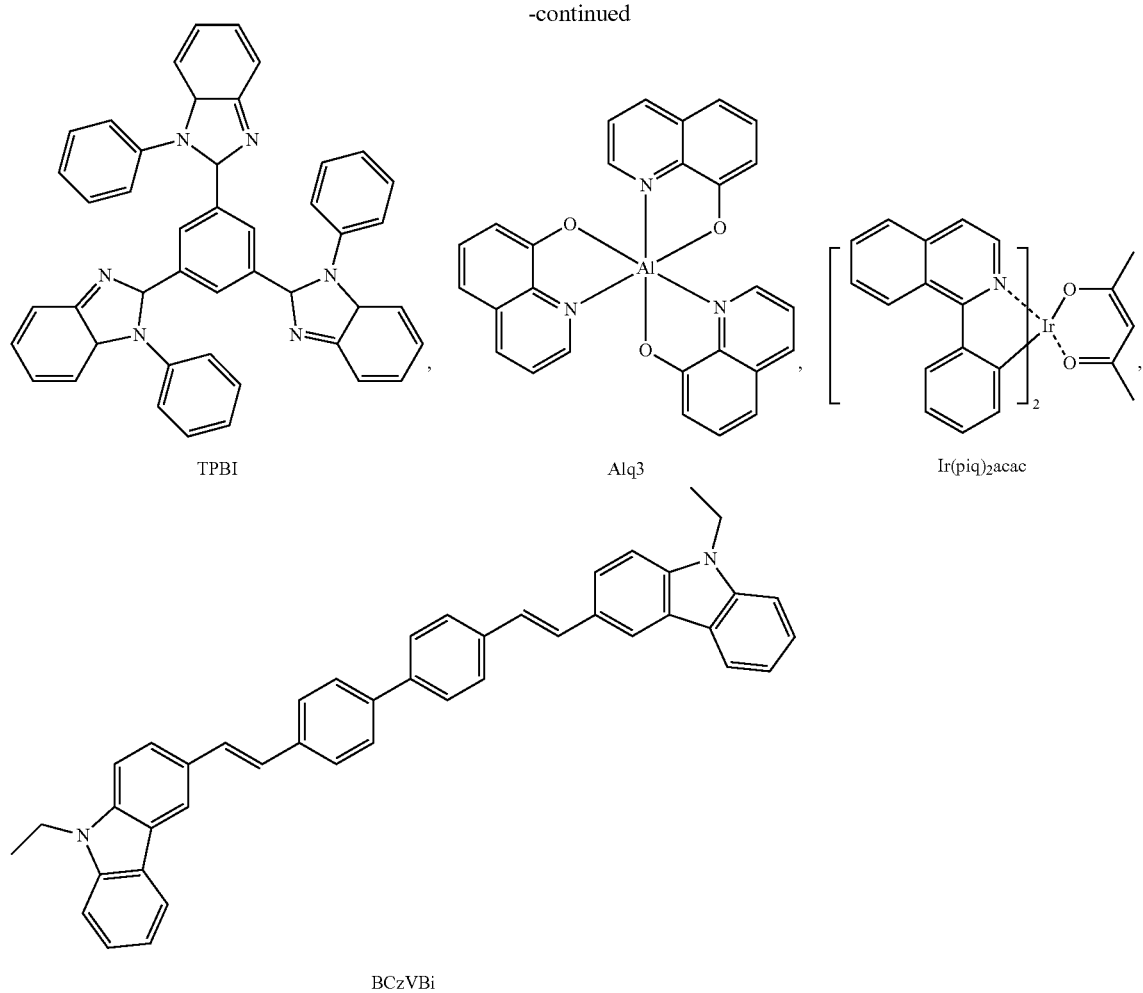

EXAMPLE 2

The preparation steps were the same as the corresponding steps in Example 1, except that in the preparation step 4), Compound P1 was replaced with Compound P2 to provide an organic light-emitting display panel N2.

EXAMPLE 3

The preparation steps were the same as the corresponding steps in Example 1, except that in the preparation step 4), Compound P1 was replaced with Compound P3 to provide an organic light-emitting display panel N3.

EXAMPLE 4

The preparation steps were the same as the corresponding steps in Example 1, except that in the preparation step 4), Compound P1 was replaced with Compound P10 and a red phosphorescent material, Ir(piq)$_2$acac, was used as the dopant material to provide an organic light-emitting display panel N4.

EXAMPLE 5

The preparation steps were the same as the corresponding steps in Example 1, except that in the preparation step 4), Compound P1 was replaced with Compound P19 and a red phosphorescent material, Ir(piq)$_2$acac, was used as the dopant material to provide an organic light-emitting display panel N5.

EXAMPLE 6

The preparation steps were the same as the corresponding steps in Example 1, except that in the preparation step 4), Compound P1 was replaced with Compound P20 to provide an organic light-emitting display panel N6.

EXAMPLE 7

The preparation steps were the same as the corresponding steps in Example 1, except that in the preparation step 4), Compound P1 was replaced with Compound P21 to provide an organic light-emitting display panel N7.

EXAMPLE 8

The preparation steps were the same as the corresponding steps in Example 1, except that in the preparation step 4), Compound P1 was replaced with Compound P24 to provide an organic light-emitting display panel N8.

EXAMPLE 9

The preparation steps were the same as the corresponding steps in Example 1, except that in the preparation step 4), Compound P1 was replaced with Compound P25 to provide an organic light-emitting display panel N9.

EXAMPLE 10

The preparation steps were the same as the corresponding steps in Example 1, except that in the preparation step 4), Compound P1 was replaced with Compound P26 and a red phosphorescent material, Ir(piq)$_2$acac, was used as the dopant material to provide an organic light-emitting display panel N10.

EXAMPLE 11

The preparation steps were the same as the corresponding steps in Example 1, except that in the preparation step 4), Compound P1 was replaced with Compound P27 and a red phosphorescent material, Ir(piq)$_2$acac, was used as the dopant material to provide an organic light-emitting display panel N11.

EXAMPLE 12

The preparation steps were the same as the corresponding steps in Example 1, except that in the preparation step 4), Compound P1 was replaced with Compound P28 to provide an organic light-emitting display panel N12.

COMPARATIVE EXAMPLE 1

The preparation steps were the same as the corresponding steps in Example 1, except that in the preparation step 4), Compound P1 was replaced with Compound C1 (4,4'-bis (9-carbazole)biphenyl) to provide an organic light-emitting display panel M1.

COMPARATIVE EXAMPLE 2

The preparation steps were the same as the corresponding steps in Example 1, except that in the preparation step 4), Compound P1 was replaced with Compound C2 (2,8-bis (diphenylphosphinyl)dibenzothiophene) to provide an organic light-emitting display panel M2.

PERFORMANCE TEST (1) Compound Simulation Calculation

The distribution of frontier molecular orbitals of the compounds of the present disclosure used in the examples was optimized and calculated at B3LYP/6-31G(d) level with Gaussian 09 package according to density functional theory (DFT). Meanwhile, the singlet energy level S1 and the triplet energy level T1 of the molecule were analog calculated based on time-dependent density functional theory (TD-DFT). The results are shown in Table 1, where $\Delta E_{ST}=S_1-T_1$, $E_g$=HOMO-LUMO, and the value of $E_g$ takes the absolute value.

(2) Performance Evaluation of Organic Light-Emitting Display Panels:

The currents of the organic light-emitting display panels as prepared in Examples and Comparative examples at different voltages were detected with Keithley 2365A Digital Nanovoltmeter. Then the current was divided by the illuminating area to obtain the current density of the organic optoelectronic device at different voltages. The brightness and radiant energy density of the organic optoelectronic devices as prepared in Examples and Comparative examples at different voltages was detected with Konicaminolta CS-2000 Spectroradiometer. According to the current density and brightness of the organic photoelectric device at different voltages, the current efficiency (Cd/A) and external quantum efficiency (EQE) at the same current density (10 mA/cm$^2$) were obtained. The results are shown in Table 2.

TABLE 1

Compound performance test results

| | Compound | HOMO(eV) | LUMO(eV) | S$_1$(eV) | T$_1$(eV) | $\Delta E_{ST}$(eV) | E$_g$(eV) |
|---|---|---|---|---|---|---|---|
| Example 1 | P1 | −5.78 | −2.55 | 2.98 | 2.74 | 0.24 | 3.23 |
| Example 2 | P2 | −5.65 | −2.35 | 3.08 | 2.85 | 0.23 | 3.30 |
| Example 3 | P3 | −5.40 | −2.46 | 2.60 | 2.52 | 0.08 | 2.84 |
| Example 4 | P10 | −5.35 | −1.88 | 3.19 | 3.04 | 0.15 | 3.47 |
| Example 5 | P19 | −5.17 | −2.54 | 3.08 | 2.86 | 0.22 | 2.63 |
| Example 6 | P20 | −5.20 | −2.65 | 2.91 | 2.80 | 0.11 | 2.55 |
| Example 7 | P21 | −5.11 | −2.85 | 2.62 | 2.59 | 0.03 | 2.26 |
| Example 8 | P24 | −4.69 | −1.79 | 2.35 | 2.26 | 0.09 | 2.90 |
| Example 9 | P25 | −5.08 | −2.58 | 2.594 | 2.592 | 0.002 | 2.50 |
| Example 10 | P26 | −4.79 | −1.96 | 2.38 | 2.20 | 0.18 | 2.83 |
| Example 11 | P27 | −4.59 | −1.72 | 2.41 | 2.33 | 0.08 | 2.87 |
| Example 12 | P28 | −5.58 | −2.36 | 3.39 | 3.23 | 0.16 | 3.22 |
| Comparative Example 1 | C1 | −5.61 | −1.76 | 3.45 | 2.60 | 0.85 | 3.85 |
| Comparative Example 2 | C2 | −6.69 | −2.99 | 3.54 | 2.96 | 0.58 | 3.70 |

As can be seen from Table 1, compared to Comparative Compounds C1 and C2, the $\Delta E_{ST}$ of all compounds of the present disclosure was less than 0.3 eV, indicating that a low energy difference between the singlet state and the triplet state was achieved. This facilitates the transformation from triplet excitons to singlet excitons and improves the utilization efficiency of triplet excitons. The compound of the present disclosure has the characteristics of thermally activated delayed fluorescence, and is suitable for use as a dopant material and a host material in the light-emitting layer of an OLED device.

Among them, the four compounds P3 and P19-P21 differed only in the positions at which D$_i$ and A$_j$ were attached to the parent core. The data shows that when attached at ortho-positions (as the case in P3 and P21), the compound had an even low $\Delta E_{ST}$ and an even better TADF performance.

TABLE 2

Luminescence performance test results of organic light-emitting display panel

| Device | Compound | | $V_{on}$[V] | $CE_{(10\ mA/cm^2)}$ (cd A$^{-1}$) | $EQE_{(max)}$(%) | Color |
|---|---|---|---|---|---|---|
| Example 1 | N1 | P1 | 4.22 | 30.2 | 16.8 | Green |
| Example 2 | N2 | P2 | 4.16 | 27.9 | 16.4 | Green |
| Example 3 | N3 | P3 | 4.12 | 33.1 | 17.9 | Green |
| Example 4 | N4 | P10 | 3.86 | 23.0 | 12.8 | Red |
| Example 5 | N5 | P19 | 4.26 | 26.8 | 15.8 | Green |
| Example 6 | N6 | P20 | 4.18 | 26.5 | 16.4 | Green |
| Example 7 | N7 | P21 | 4.12 | 29.8 | 17.6 | Green |
| Example 8 | N8 | P24 | 3.76 | 23.6 | 13.5 | Red |
| Example 9 | N9 | P25 | 4.14 | 35.2 | 19.6 | Green |
| Example 10 | N10 | P26 | 3.70 | 23.2 | 12.8 | Red |
| Example 11 | N11 | P27 | 3.82 | 24.0 | 14.6 | Red |
| Example 12 | N12 | P28 | 4.22 | 31.8 | 17.4 | Green |
| Comparative Example 1 | M1 | C1 | 4.08 | 21.1 | 12.4 | Green |
| Comparative Example 2 | M2 | C2 | 4.16 | 20.6 | 11.8 | Green |

As can be seen from Table 2, dopant devices using Compounds P1-P28 of the present disclosure as the host material and Ir(piq)$_2$acac and Ir(ppy)$_3$ as the dopant material achieved a maximum external quantum efficiency of 14.6% (red light) or 19.6% (green light), indicating that the compound of the present disclosure can be used as a host material of a phosphorescent material, and had a higher external quantum efficiency than compounds in Comparative Examples which had a $\Delta E_{ST}$ of greater than 0.3 eV.

By comparing Examples 3 and 5-7, it was shown that the compounds of the present disclosure had a higher maximum external quantum efficiency when the $D_i$ and $A_j$ groups were attached at ortho-positions (as the case in Example 3 and Example 7).

EXAMPLE 13

In this embodiment, the compound of the present disclosure was used as a dopant material to prepare an organic light-emitting display panel. The specific preparation steps are as follows.

An anode substrate with an ITO film having a thickness of 100 nm was ultrasonically washed with distilled water, acetone, and isopropanol, dried in an oven, exposed to UV for 30 minutes for surface treatment, and then transferred to a vacuum evaporation chamber. Each layer of film was deposited by evaporation at a vacuum degree of $2\times10^{-6}$ Pa:

5 nm-thick HATCN was deposited by evaporation to form a hole injection layer; 40 nm-thick N,N'-diphenyl-N,N'-(1-naphthyl)-1,1'-biphenyl-4,4'-diamine (α-NPD) was deposited by evaporation; and then 10 nm-thick 4,4',4''-tris(carbazol-9-yl)triphenylamine (TCTA) was deposited by evaporation to form a hole transport layer (HTL). On the hole transport layer, Compound P1 of the present disclosure was used as a dopant material (guest material) of the light-emitting layer, and 3,3'-bis(N-carbazolyl)-1,1'-biphenyl (mCBP) was used as a host material of the light-emitting layer. The dopant material and host material were simultaneously deposited by evaporation to form a light-emitting layer having a thickness of 30 nm. Then, diphenyl[4-(triphenylsilyl)phenyl]phosphine oxide (TSPO1) was deposited on the light-emitting layer by evaporation to form a hole blocking layer (HBL) having a thickness of 5 nm. 4,7-Diphenyl-1,10-phenanthroline (Bphen) was deposited on the hole blocking layer by evaporation to form an electron transport layer (ETL) having a thickness of 30 nm. 2.5 nm-thick LiF and 100 nm-thick Al were deposited sequentially on the electron transport layer by evaporation and were used as an electron injection layer (EIL) and a cathode, respectively. Thus an organic light-emitting display panel N13 was prepared.

EXAMPLE 14

The preparation steps were the same as the corresponding steps in Example 13, except that Compound P1 was replaced with Compound P2 to provide an organic light-emitting display panel N14.

EXAMPLE 15

The preparation steps were the same as the corresponding steps in Example 13, except that Compound P1 was replaced with Compound P3 to provide an organic light-emitting display panel N15.

EXAMPLE 16

The preparation steps were the same as the corresponding steps in Example 13, except that Compound P1 was replaced with Compound P10 to provide an organic light-emitting display panel N16.

EXAMPLE 17

The preparation steps were the same as the corresponding steps in Example 13, except that Compound P1 was replaced with Compound P19 to provide an organic light-emitting display panel N17.

EXAMPLE 18

The preparation steps were the same as the corresponding steps in Example 13, except that Compound P1 was replaced with Compound P20 to provide an organic light-emitting display panel N18.

EXAMPLE 19

The preparation steps were the same as the corresponding steps in Example 13, except that Compound P1 was replaced with Compound P21 to provide an organic light-emitting display panel N19.

EXAMPLE 20

The preparation steps were the same as the corresponding steps in Example 13, except that Compound P1 was replaced with Compound P24 to provide an organic light-emitting display panel N20.

EXAMPLE 21

The preparation steps were the same as the corresponding steps in Example 13, except that Compound P1 was replaced with Compound P25 to provide an organic light-emitting display panel N21.

EXAMPLE 22

The preparation steps were the same as the corresponding steps in Example 13, except that Compound P1 was replaced with Compound P26 to provide an organic light-emitting display panel N22.

EXAMPLE 23

The preparation steps were the same as the corresponding steps in Example 13, except that Compound P1 was replaced with Compound P27 to provide an organic light-emitting display panel N23.

EXAMPLE 24

The preparation steps were the same as the corresponding steps in Example 13, except that Compound P1 was replaced with Compound P28 to provide an organic light-emitting display panel N24.

COMPARATIVE EXAMPLE 3

The preparation steps were the same as the corresponding steps in Example 13, except that in the preparation step 4), Compound P1 was replaced with Compound C3 (BCzVBi) to provide an organic light-emitting display panel M3.

The organic light-emitting display panels of Examples 13 to 23 and Comparative Example 3 were tested in accordance with the method of Performance test (2) as described above, and the results are shown in Table 3.

It can be seen from Table 3 that the EQE(max) of (dopant) devices N13, N14, N16, N17, N18 and N24 was significantly higher than that of the reference device M3 which used the classical blue light-emitting material BCzVBi as the fluorescent dopant. This is mainly due to the TADF characteristics of P1, P2, P10, P19, P20 and P28 per se. They can emit light by using triplet excitons whose transition is forbidden in conventional fluorescent molecules (such as BCzVBi), thereby improving the efficiency of a device.

By comparing Examples 15 and 17-19, it was shown that the compounds of the present disclosure had a higher maximum external quantum efficiency when the $D_i$ and $A_j$ groups were attached at ortho-positions (as the case in Example 15 and Example 19).

EXAMPLE 25

In this embodiment, the compound of the present disclosure was used as both a guest material and a host material to prepare an organic light-emitting display panel. The specific preparation steps are as follows.

An anode substrate with an ITO film having a thickness of 100 nm was ultrasonically washed with distilled water, acetone, and isopropanol, dried in an oven, exposed to UV for 30 minutes for surface treatment, and then transferred to a vacuum evaporation chamber. Each layer of film was deposited by evaporation at a vacuum degree of $2 \times 10^{-6}$ Pa:

5 nm-thick HATCN was deposited by evaporation to form a hole injection layer; 40 nm-thick N,N'-diphenyl-N,N'-(1-naphthyl)-1,1'-biphenyl-4,4'-diamine (α-NPD) was deposited by evaporation; and then 10 nm-thick 4,4',4"-tris(carbazol-9-yl)triphenylamine (TCTA) was deposited by evaporation to form a hole transport layer (HTL). On the hole transport layer, the Compound P1 of the present disclosure was deposited by evaporation to form a light-emitting layer having a thickness of 30 nm. Then, diphenyl [4-(triphenylsilyl)phenyl]phosphine oxide (TSPO1) was deposited on the light-emitting layer by evaporation to form a hole blocking layer (HBL) having a thickness of 5 nm. 4,7-Diphenyl-1,10-phenanthroline (Bphen) was deposited on the hole blocking layer by evaporation to form an electron transport layer (ETL) having a thickness of 30 nm. 2.5 nm-thick LiF and 100 nm-thick Al were deposited sequentially on the electron transport layer by evaporation

TABLE 3

Luminescence performance test results of organic light-emitting display panel

| | Device | Compound | $V_{on}$[V] | $CE_{(10\ mA/cm^2)}$ (cd A$^{-1}$) | $EQE_{(max)}$(%) | Color |
|---|---|---|---|---|---|---|
| Example 13 | N13 | P1 | 4.72 | 18.9 | 10.6 | Blue |
| Example 14 | N14 | P2 | 4.68 | 21.5 | 11.8 | Blue |
| Example 15 | N15 | P3 | 4.26 | 34.4 | 18.5 | Green |
| Example 16 | N16 | P10 | 4.45 | 17.2 | 9.8 | Blue |
| Example 17 | N17 | P19 | 4.56 | 17.8 | 10.4 | Blue |
| Example 18 | N18 | P20 | 4.68 | 17.2 | 9.6 | Blue |
| Example 19 | N19 | P21 | 4.48 | 29.5 | 16.4 | Green |
| Example 20 | N20 | P24 | 3.84 | 23.1 | 13.6 | Red |
| Example 21 | N21 | P25 | 4.24 | 28.0 | 15.6 | Green |
| Example 22 | N22 | P26 | 3.96 | 18.4 | 10.4 | Red |
| Example 23 | N23 | P27 | 4.26 | 25.0 | 15.2 | Red-green |
| Example 24 | N24 | P28 | 4.60 | 22.9 | 12.4 | Blue |
| Comparative Example 3 | M3 | C3 | 4.80 | 7.2 | 4.8 | Blue |

EXAMPLE 26

The preparation steps were the same as the corresponding steps in Example 25, except that Compound P1 was replaced with Compound P2 to provide an organic light-emitting display panel N26.

EXAMPLE 27

The preparation steps were the same as the corresponding steps in Example 25, except that Compound P1 was replaced with Compound P3 to provide an organic light-emitting display panel N27.

EXAMPLE 28

The preparation steps were the same as the corresponding steps in Example 25, except that Compound P1 was replaced with Compound P10 to provide an organic light-emitting display panel N28.

EXAMPLE 29

The preparation steps were the same as the corresponding steps in Example 25, except that Compound P1 was replaced with Compound P19 to provide an organic light-emitting display panel N29.

EXAMPLE 30

The preparation steps were the same as the corresponding steps in Example 25, except that Compound P1 was replaced with Compound P20 to provide an organic light-emitting display panel N30.

EXAMPLE 31

The preparation steps were the same as the corresponding steps in Example 25, except that Compound P1 was replaced with Compound P21 to provide an organic light-emitting display panel N31.

EXAMPLE 32

The preparation steps were the same as the corresponding steps in Example 25, except that Compound P1 was replaced with Compound P24 to provide an organic light-emitting display panel N32.

EXAMPLE 33

The preparation steps were the same as the corresponding steps in Example 25, except that Compound P1 was replaced with Compound P25 to provide an organic light-emitting display panel N33.

EXAMPLE 34

The preparation steps were the same as the corresponding steps in Example 25, except that Compound P1 was replaced with Compound P26 to provide an organic light-emitting display panel N34.

EXAMPLE 35

The preparation steps were the same as the corresponding steps in Example 25, except that Compound P1 was replaced with Compound P27 to provide an organic light-emitting display panel N35.

EXAMPLE 36

The preparation steps were the same as the corresponding steps in Example 25, except that Compound P1 was replaced with Compound P28 to provide an organic light-emitting display panel N36.

COMPARATIVE EXAMPLE 4

The preparation steps were the same as the corresponding steps in Example 25, except that in the preparation steps, Compound P1 was replaced with Compound C3 (BCzVBi) to provide an organic light-emitting display panel M4.

The organic light-emitting display panels of Examples 25 to 36 and Comparative Example 4 were tested in accordance with the method of Performance test (2) as described above, and the results are shown in Table 4.

TABLE 4

| | Device | Compound | $V_{on}$[V] | $CE_{(10\ mA/cm^2)}$ (cd $A^{-1}$) | $EQE_{(max)}$(%) | Color |
|---|---|---|---|---|---|---|
| Example 25 | N25 | P1 | 4.80 | 9.6 | 5.6 | Blue |
| Example 26 | N26 | P2 | 4.69 | 12.2 | 6.8 | Blue |
| Example 27 | N27 | P3 | 4.54 | 23.8 | 14.5 | Green |
| Example 28 | N28 | P10 | 4.76 | 13.6 | 8.0 | Blue |
| Example 29 | N29 | P19 | 4.82 | 10.8 | 6.8 | Blue |
| Example 30 | N30 | P20 | 4.68 | 11.5 | 7.2 | Blue |
| Example 31 | N31 | P21 | 4.60 | 20.4 | 11.2 | Green |
| Example 32 | N32 | P24 | 4.23 | 17.8 | 9.6 | Red |
| Example 33 | N33 | P25 | 4.65 | 21.8 | 12.6 | Green |
| Example 34 | N34 | P26 | 4.14 | 15.5 | 8.4 | Red |
| Example 35 | N35 | P27 | 4.82 | 17.1 | 10.2 | Red-green |
| Example 36 | N36 | P28 | 4.86 | 15.0 | 7.9 | Blue |
| Comparative Example 4 | M4 | C3 | 5.04 | 3.0 | 1.67 | Blue |

As can be seen from Table 4, compared to Compound C3 of Comparative Example 4, the devices prepared using P1-P28 as light-emitting materials by a non-doped vacuum evaporation method achieved a maximum external quantum efficiency of 14.5%. This indicated that, as a result of the introduction of the dibenzothiophene group, the interaction between the $D_i$ unit and the $A_j$ unit within the molecule was more intense, the molecular distortion strength was increased, and a larger dihedral angle was formed, thereby separating the HOMO orbit from the LUMO orbit effectively, attenuating the exciton quenching problem caused by π-π stacking, and achieving a higher photoluminescence quantum yield (PLQY) while allowing the molecule to maintain a certain degree of rigidity, and thereby obtaining more satisfactory performance for devices.

By comparing Examples 27 and 29-31, it was shown that the compounds of the present disclosure had a higher maximum external quantum efficiency when the $D_i$ and $A_j$ groups were attached at ortho-positions (as the case in Example 27 and Example 31).

Figure 2:
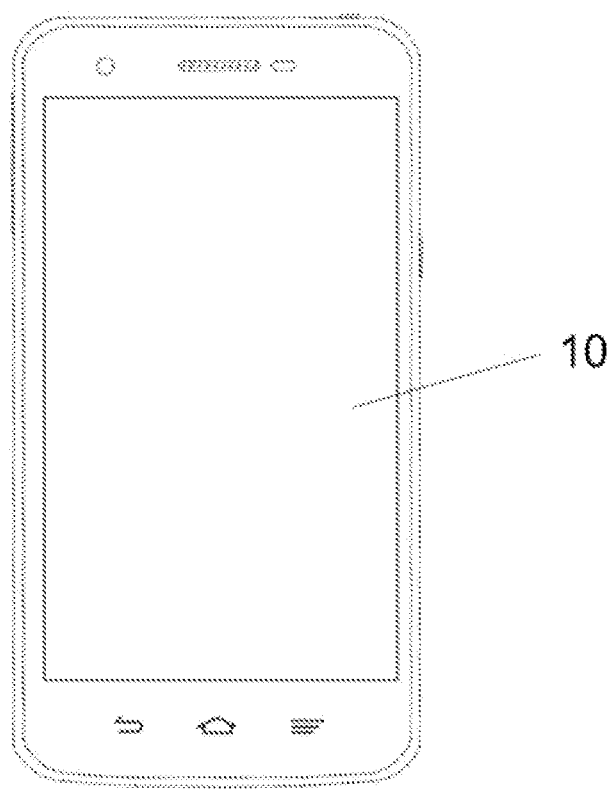
FIG. 2 shows a schematic view of an organic light-emitting display device provided in an embodiment of the present disclosure; wherein: 10—mobile phone display screen.

Yet another aspect of an embodiment of the present disclosure provides an organic light-emitting display device, which comprises the organic light-emitting display panel as described above. The organic light-emitting display device may be any electronic device having a display function such as a touch display screen, a mobile phone, a tablet computer, a notebook computer, an electronic paper book, a television, a VR or AR helmet or a smart watch. FIG. 2 shows a schematic view of an organic light-emitting display device provided in an example of the present disclosure, wherein 1 represents a mobile phone display screen.

The applicant states that detailed equipment and process of the present application are demonstrated in the present application through the above embodiments, however, the present application is not limited to the above detailed equipment and process, that is, it does not mean that the present application must rely on the above detailed equipment and process to implement. It should be apparent to those skilled in the art that, for any improvement of the present application, the equivalent replacement of the raw materials of the present application, the addition of auxiliary components, and the selection of specific modes, etc., will all fall within the protection scope and the disclosure scope of the present application.

What is claimed is:

1. A compound of Formula I:
wherein Formula I is:

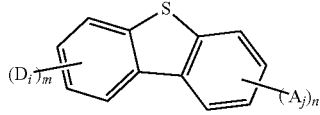

wherein in Formula I, $D_i$ is any one selected from the group consisting of a substituted or unsubstituted arylamino group, a substituted or unsubstituted carbazole group, a substituted or unsubstituted carbazole derivative group, a substituted or unsubstituted acridine group, and a substituted or unsubstituted acridine derivative group;

wherein in Formula I, $A_j$ is any one selected from an aryl group including an electron-withdrawing group;

wherein the electron-withdrawing group includes any one or a combination of at least two selected from the group consisting of carbonyl, a sulfone group, a six-membered phosphorus heterocyclic group containing phosphoryl, a boron atom and an imide;

wherein in Formula I, m is an integer from 1 to 4, and n is an integer from 1 to 4;

wherein $A_j$ is any one selected from the group consisting of

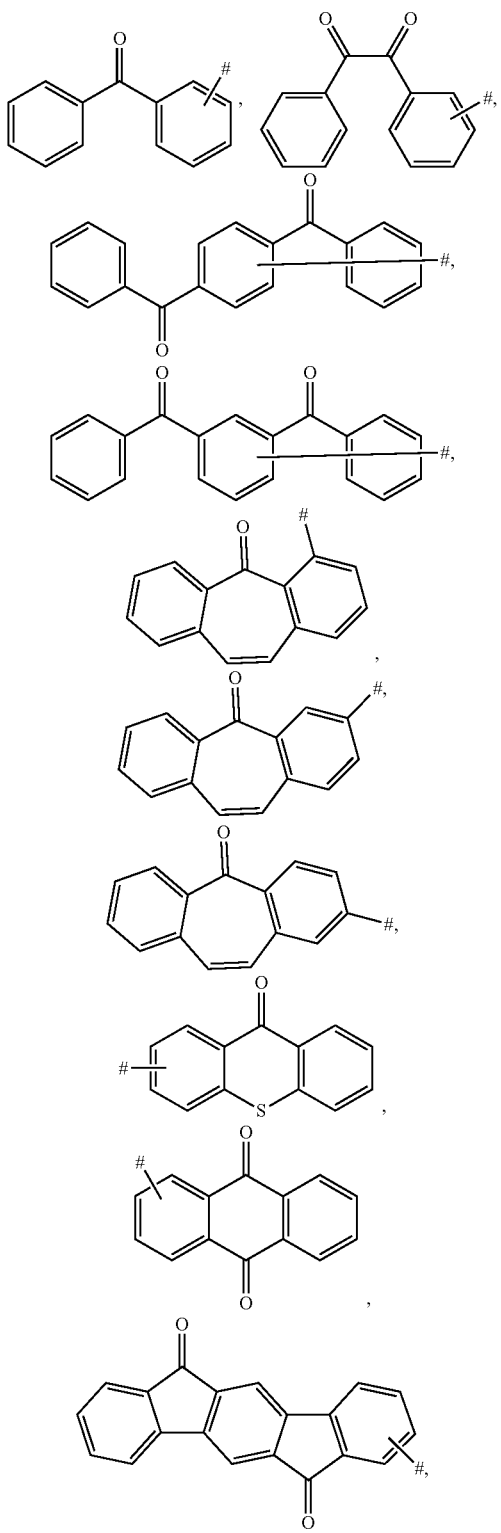

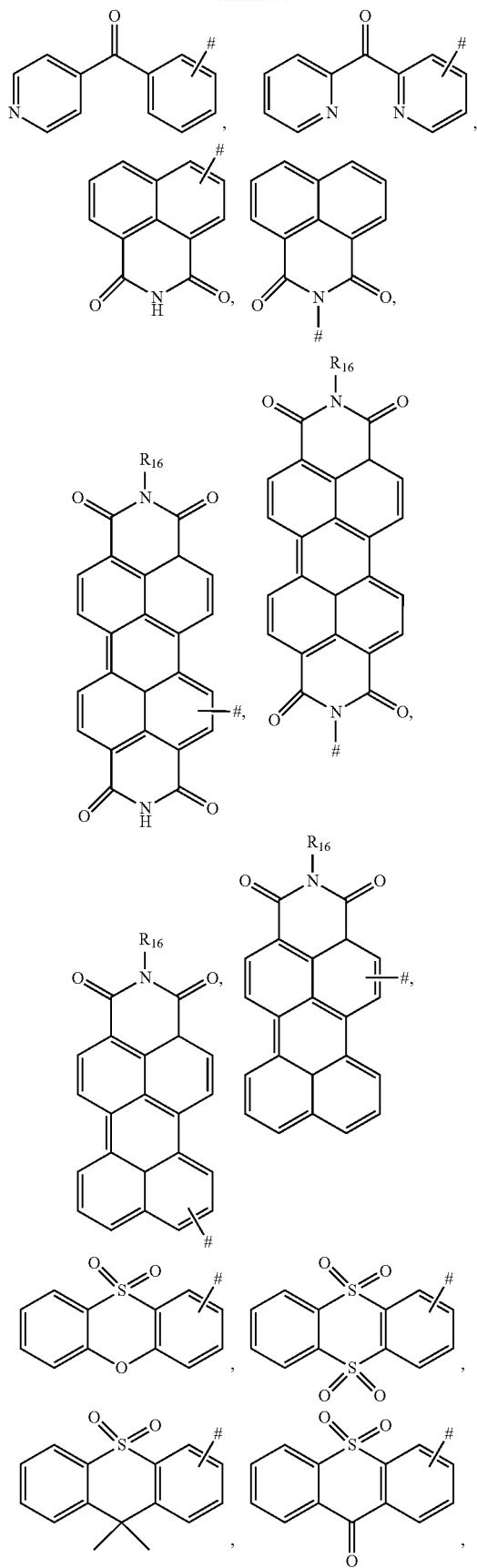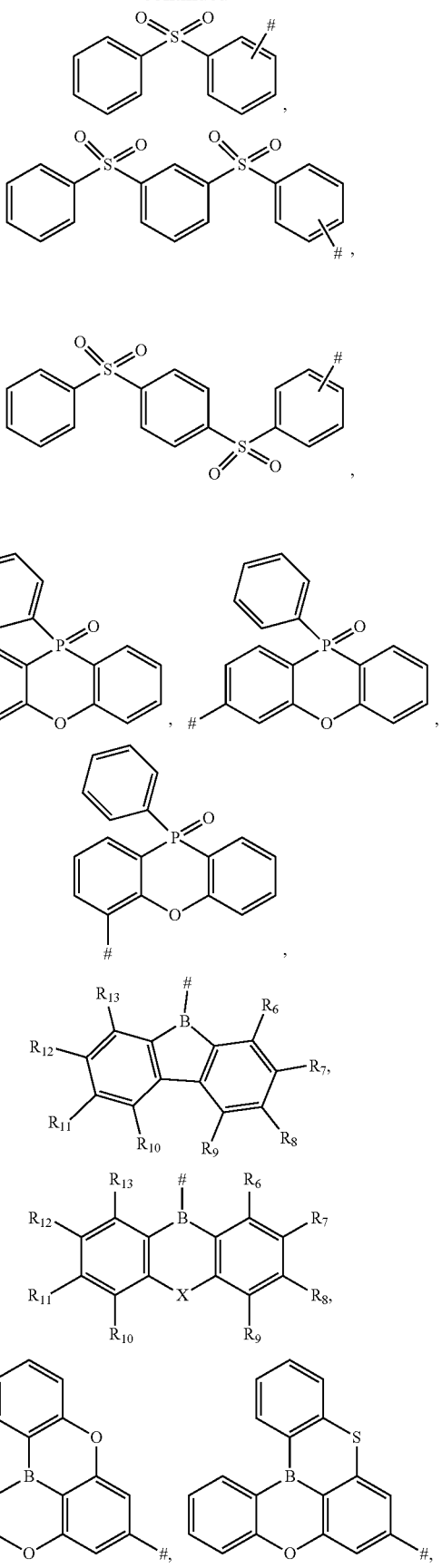

-continued

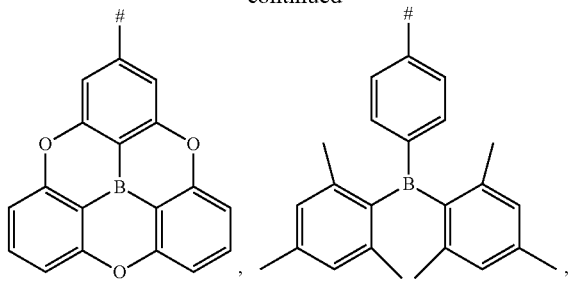

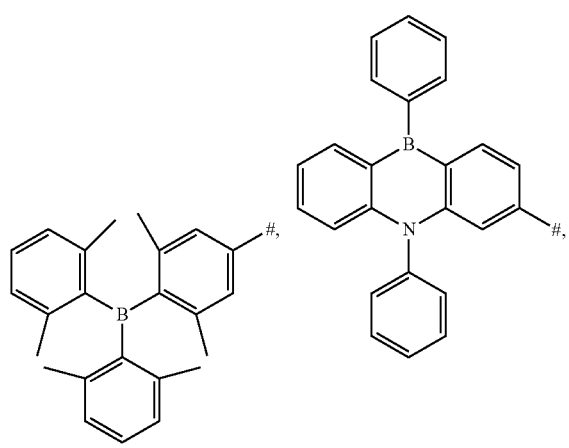

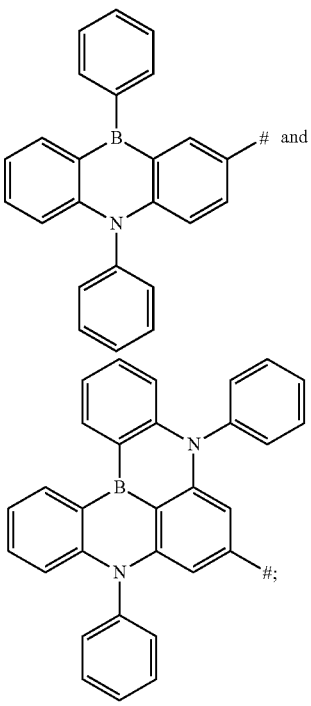

wherein # indicates a bonding position;
wherein $R_{16}$ is any one selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl;

X is any one selected from the group consisting of

an oxygen atom, and a sulfur atom; and
wherein $R_6$, $R_7$, $R_8$, $R_9$, $R_{10}$, $R_{11}$, $R_{12}$, $R_{13}$, $R_{14}$ and $R_{15}$ are each independently any one selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl.

2. The compound according to claim 1, wherein m≥n.

3. The compound according to claim 1, wherein the compound is a structure of Formula II or a structure of Formula III;
wherein Formula II is:

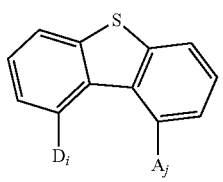

wherein Formula III is:

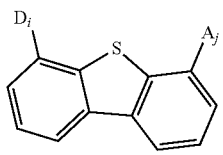

wherein $D_i$ is any one selected from the group consisting of a substituted or unsubstituted acylamino group, a substituted or unsubstituted carbazole group, a substituted or unsubstituted carbazole derivative group, a substituted or unsubstituted acridine group, and a substituted or unsubstituted acridine derivative group; and
wherein $A_j$ is any one selected from an aryl group containing an electron-withdrawing group;
wherein the electron-withdrawing group includes any one or a combination of at least two selected from the group consisting of carbonyl, a sulfone group, phosphoryl, a boron atom and an imide.

4. The compound according to claim 1, wherein D is selected from the group

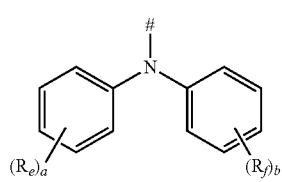

wherein # indicates a bonding position;
wherein a and b each is independently selected from an integer from 0 to 5, and
wherein $R_c$ and $R_f$ each is independently selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl.

5. The compound according to claim 1, wherein $D_i$ is any one selected from the group consisting of

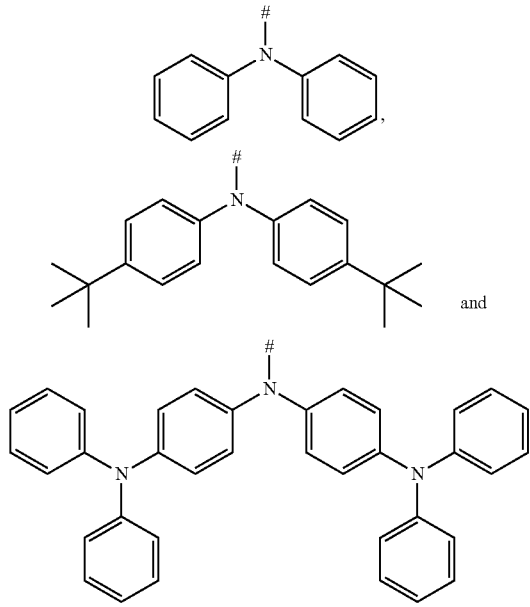

wherein # indicates a bonding position.

6. The compound according to claim 1, wherein $D_i$ is any one selected from the group consisting of

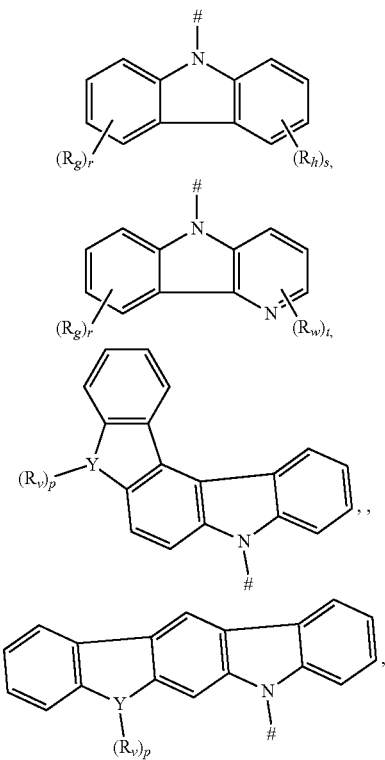

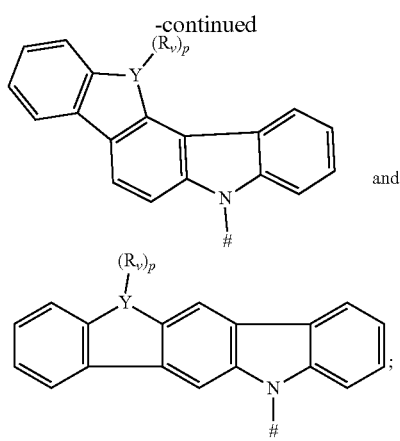

wherein # indicates a bonding position;

wherein r and s each is independently selected from an integer from 0 to 4, t is an integer from 0 to 3, p is an integer from 0 to 2, Y is any one selected from the group consisting of a carbon atom, a nitrogen atom, an oxygen atom, a sulfur atom, and a silicon atom; and wherein $R_g$, $R_h$, $R_w$ and $R_v$ are each independently any one selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl.

7. The compound according to claim 1, wherein $D_i$ is any one selected from the group consisting of

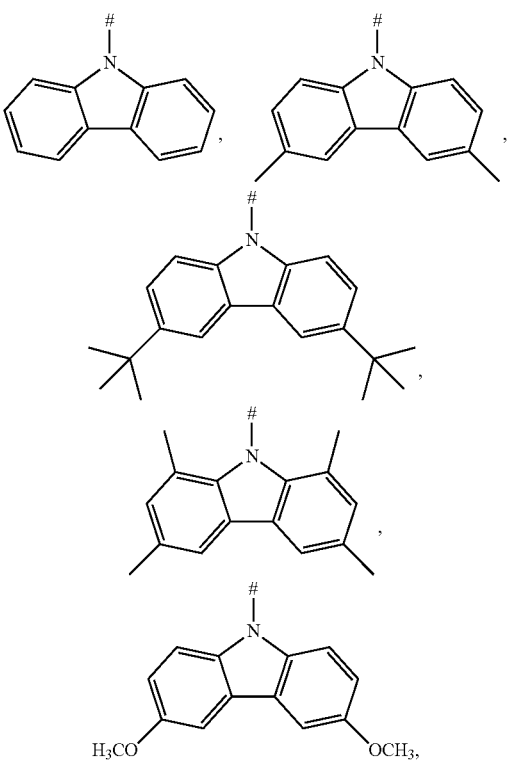

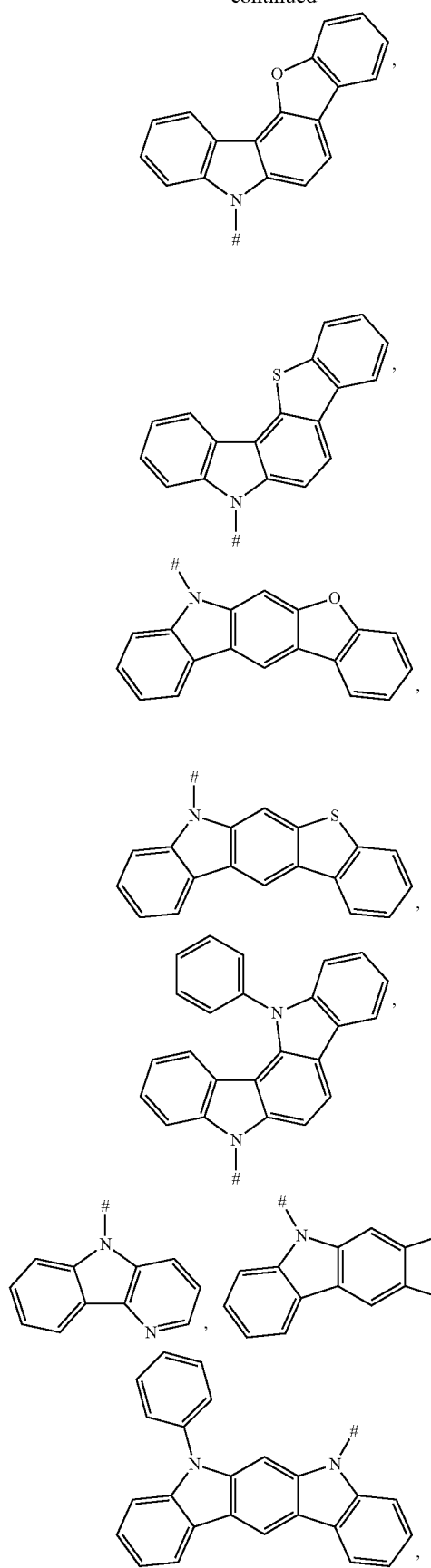
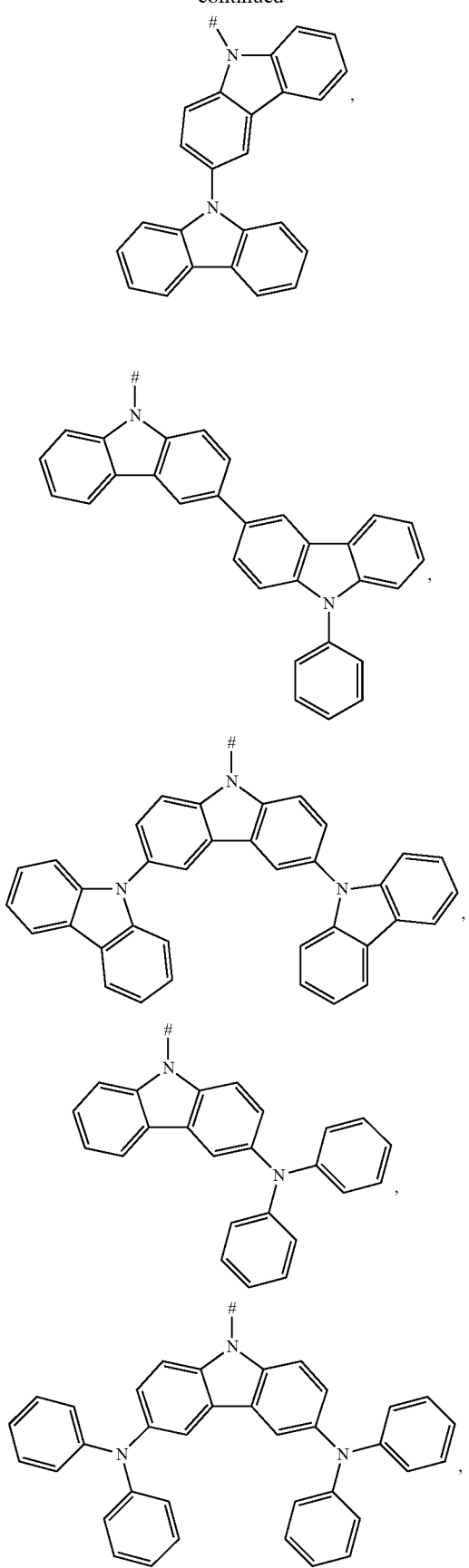

-continued

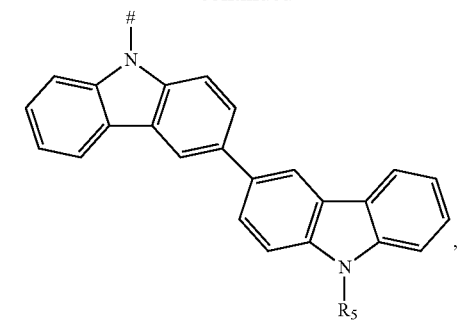

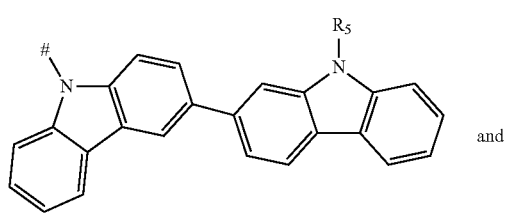

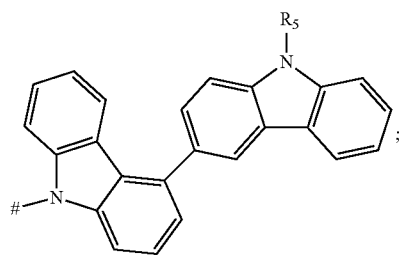

wherein # indicates a bonding position; and wherein $R_5$ is any one selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl.

8. The compound according to claim 1, wherein $D_i$ is any one selected from the group consisting of

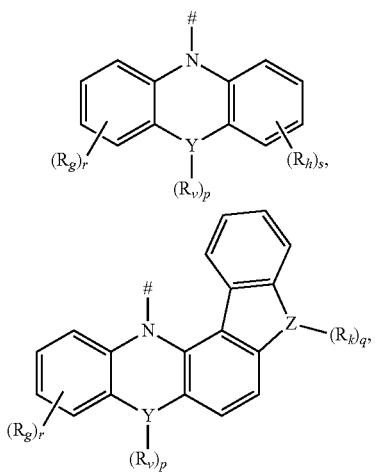

-continued

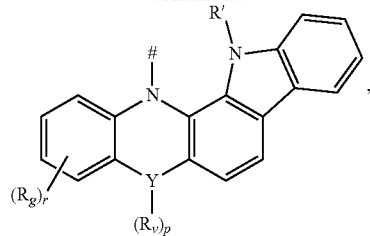

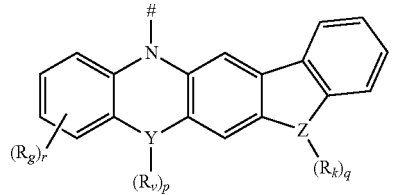

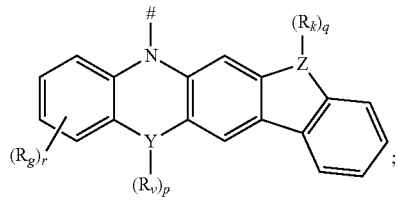

wherein # indicates a bonding position;

wherein r and s are each independently selected from an integer from 0 to 4, p and q are each independently selected from an integer from 0 to 2, Y and Z are each independently any one selected from the group consisting of a carbon atom, a nitrogen atom, an oxygen atom, a sulfur atom, and a silicon atom; and wherein R', $R_g$, $R_v$, $R_h$ and $R_k$ are each independently any one selected from the group consisting of substituted or unsubstituted C1-C20 alkyl, substituted or unsubstituted C1-C20 alkoxy, substituted or unsubstituted C6-C30 aryl, and substituted or unsubstituted C3-C30 heteroaryl.

9. The compound according to claim 1, wherein $D_i$ is any one selected from the group consisting of

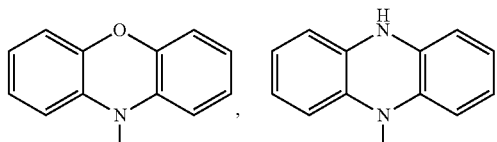

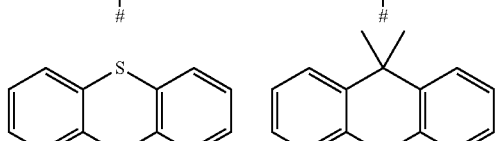

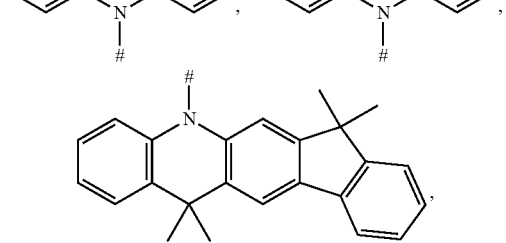

-continued

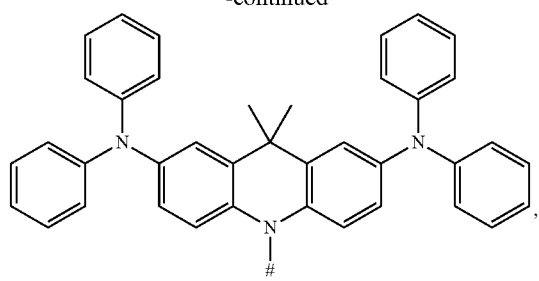

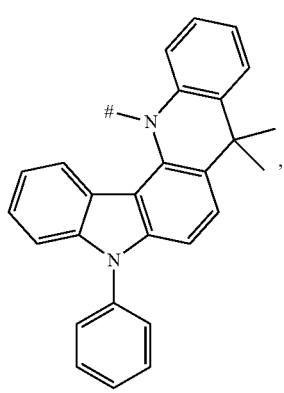

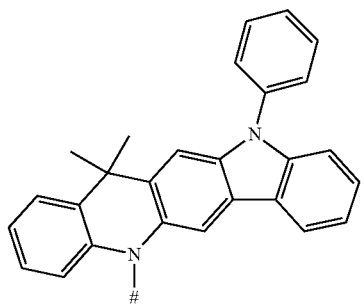 and

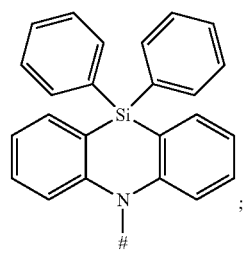

wherein # indicates a bonding position.

10. The compound according to claim 1, wherein m is 1 and n is 1.

11. The compound according to claim 1, wherein the compound includes an energy level difference between a singlet level and a triplet level and $\Delta E_{st}=E_{S1}-E_{T1}\leq 0.3$ eV.

12. The compound according to claim 1, wherein the compound is any one selected from the group consisting of compounds P1 to P15 and P17 to P28 as follows:

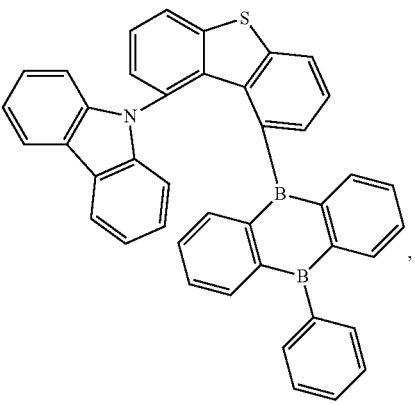
P1

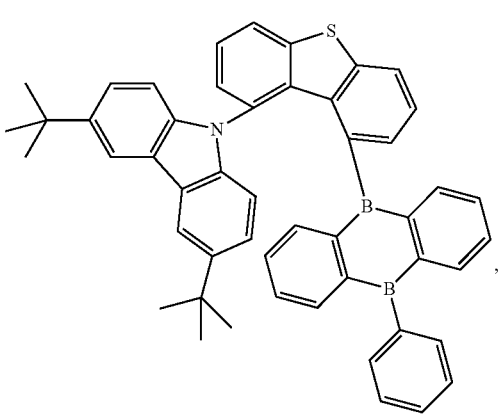
P2

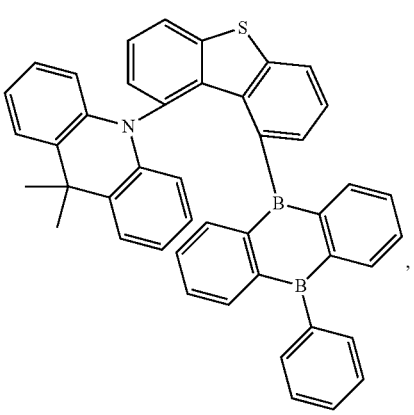
P3

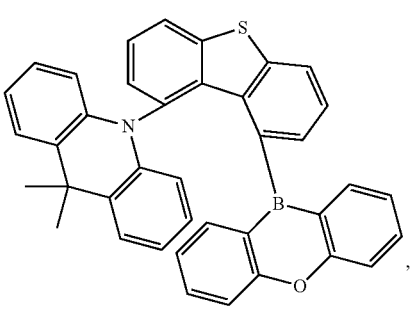
P4

P5
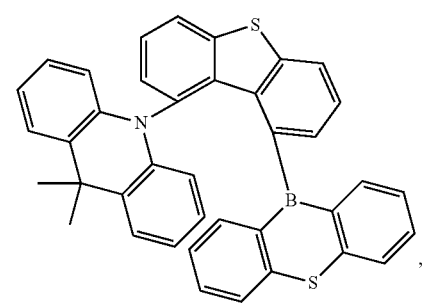
P6
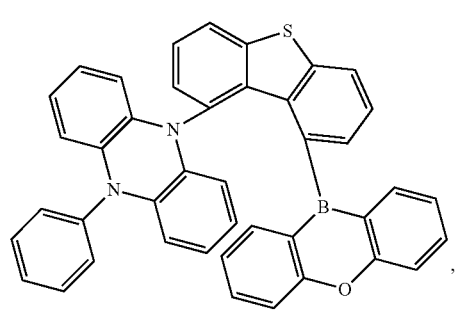
P7
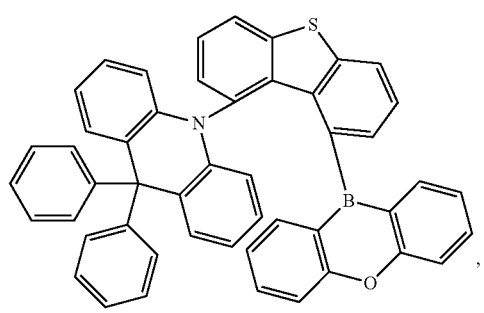
P8
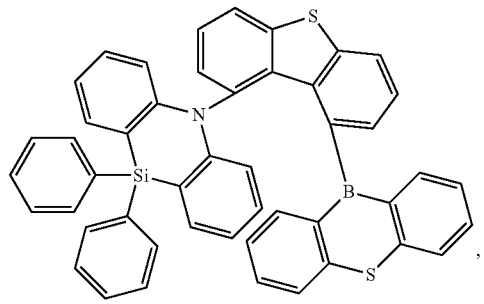
P9
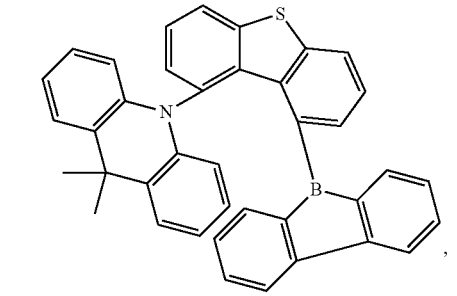
P10
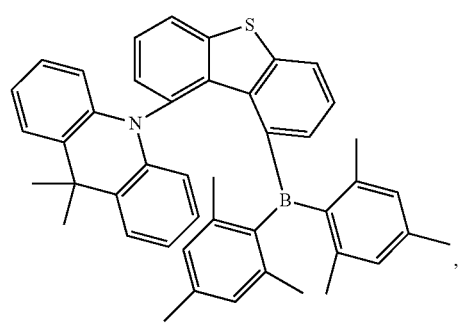
P11
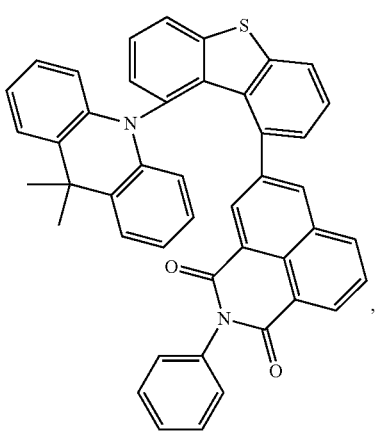
P12
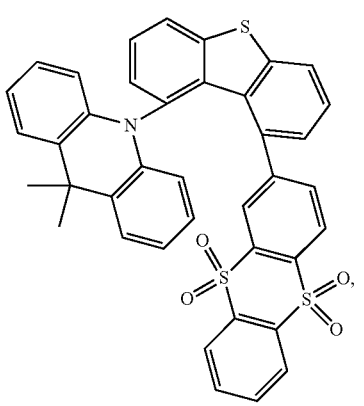
P13
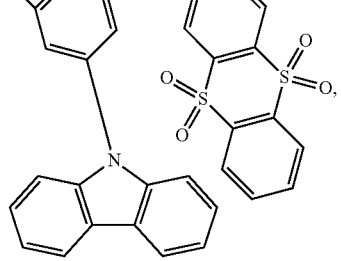

-continued
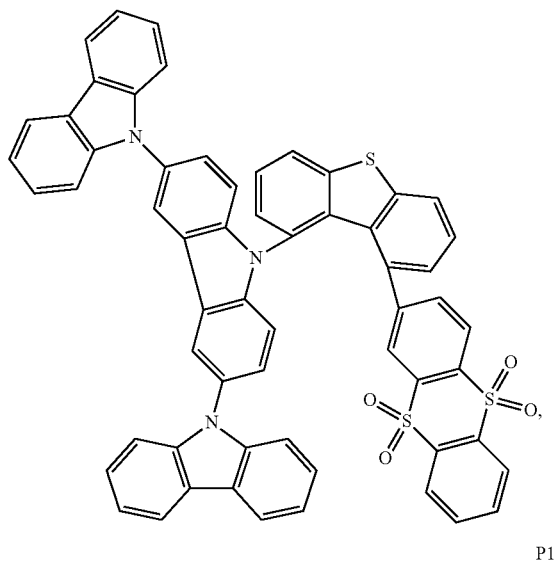
P14
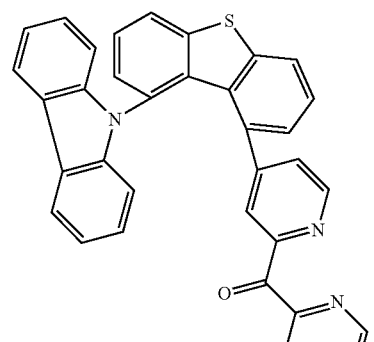
P15
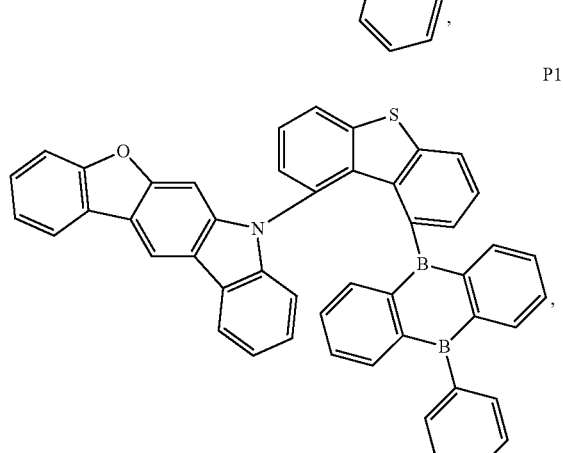
P17
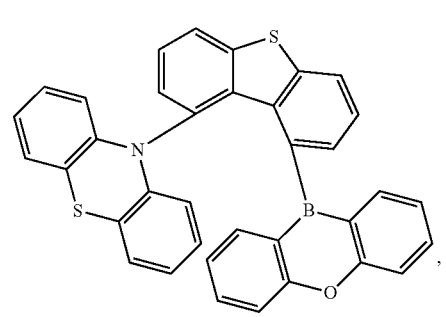
P18
-continued
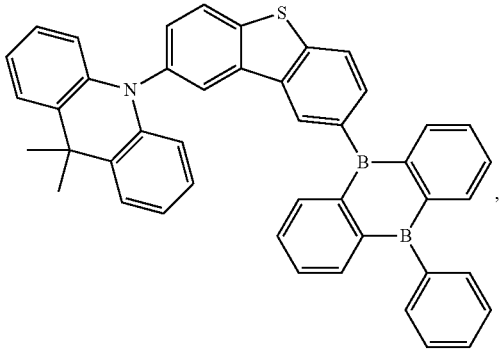
P19
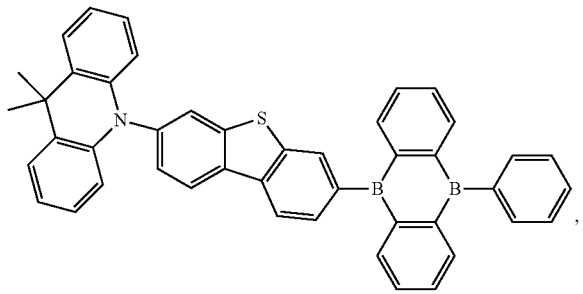
P20
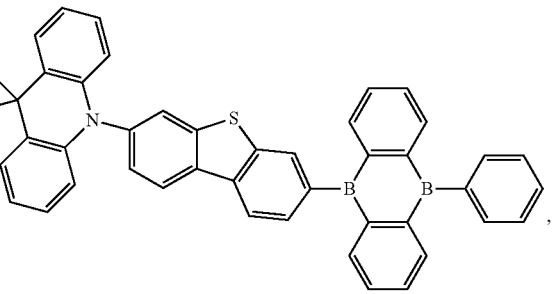
P21
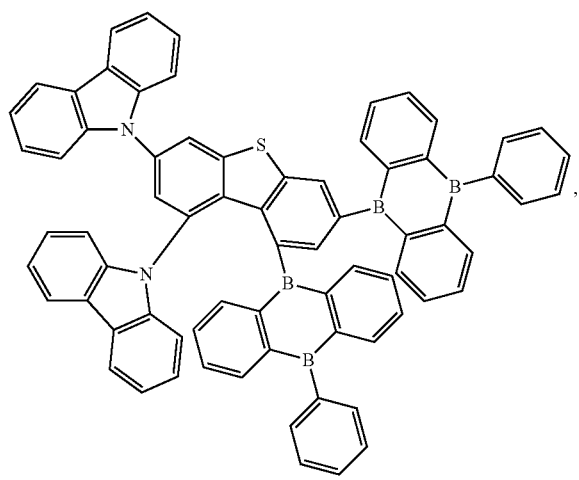
P22

P23

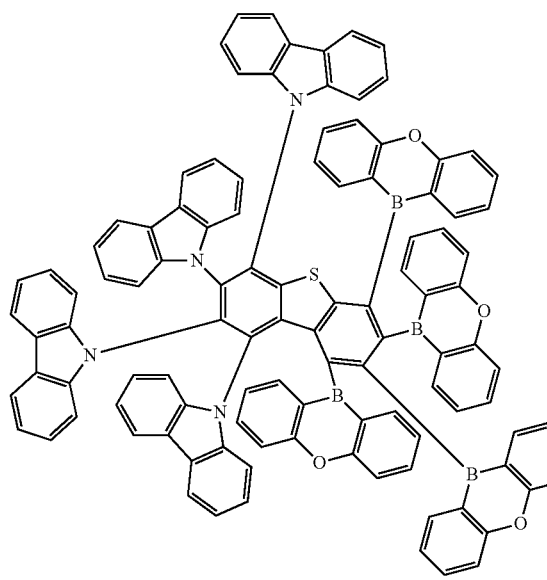

P24

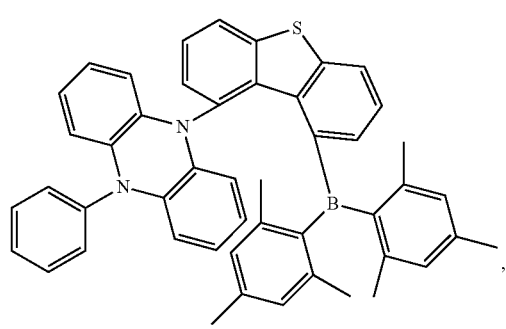

P25

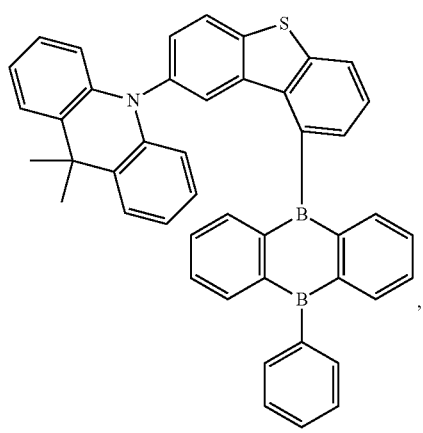

P26

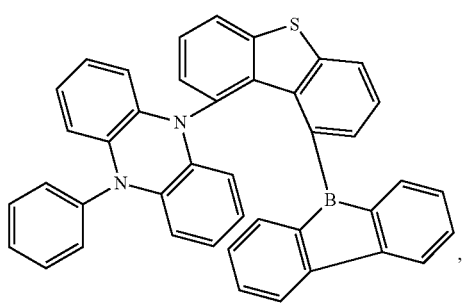

P27

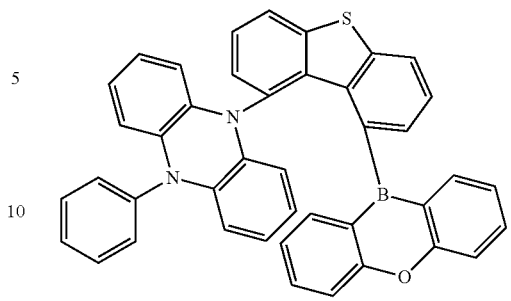

and

P28

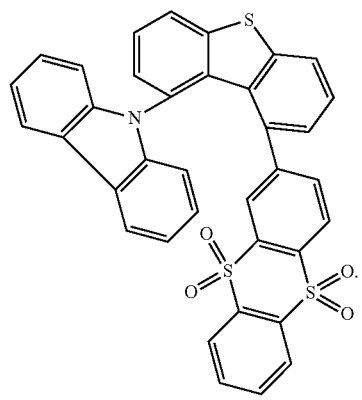

13. A light-emitting material comprising any one or a combination of at least two of the compounds according to claim 1, wherein the compound having the structure of Formula I.

14. An organic light-emitting display device comprising an anode and a cathode disposed opposite to each other, and an organic layer disposed between the anode and the cathode;
wherein a material of the organic layer comprises any one or a combination of at least two of the compounds according to claim 1, wherein the compound having the structure of Formula I.

15. The organic light-emitting display device according to claim 14, wherein the organic light-emitting display device further comprises a cap layer deposed on the side of the cathode facing away from the anode, wherein the material of the cap layer comprises any one or a combination of at least two of the compounds according to Formula I.

16. The organic light-emitting display device according to claim 14, wherein the organic layer comprises any one or a combination of at least two of the group consisting of a hole transport layer, a hole injection layer, an electron blocking layer, a light-emitting layer, a hole blocking layer, an electron transport layer, and an electron injection layer.

17. The organic light-emitting display device according to claim 14, wherein the compound as a guest material or host material in the organic layer.

18. The organic light-emitting display device according to claim 14, wherein the organic layer comprises a light-emitting layer, wherein the compound is a host material or guest material in the light-emitting layer.

19. The organic light-emitting display device according to claim 14, wherein the organic light-emitting display device is an organic light-emitting display panel.

* * * * *